(12) United States Patent
Chen

(10) Patent No.: US 11,544,893 B2
(45) Date of Patent: Jan. 3, 2023

(54) SYSTEMS AND METHODS FOR DATA DELETION

(71) Applicant: WUHAN UNITED IMAGING HEALTHCARE CO., LTD., Wuhan (CN)

(72) Inventor: Ke Chen, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 102 days.

(21) Appl. No.: 16/888,819

(22) Filed: May 31, 2020

(65) Prior Publication Data
US 2020/0294303 A1 Sep. 17, 2020

Related U.S. Application Data

(63) Continuation of application No. 15/638,600, filed on Jun. 30, 2017, now Pat. No. 10,672,179, which is a (Continued)

(30) Foreign Application Priority Data

Dec. 30, 2015 (CN) .......................... 201511022787.2
Jul. 11, 2016 (CN) .......................... 201610541853.5

(51) Int. Cl.
*G06T 15/08* (2011.01)
*G06T 11/40* (2006.01)
(Continued)

(52) U.S. Cl.
CPC ................ *G06T 15/08* (2013.01); *G06T 7/38* (2017.01); *G06T 11/003* (2013.01); *G06T 11/40* (2013.01);
(Continued)

(58) Field of Classification Search
CPC ....... G06F 3/0608; G06F 17/10; G06T 15/08; G06T 7/38; G06T 19/00; G06T 11/003;
(Continued)

(56) References Cited

U.S. PATENT DOCUMENTS 5,832,522 A * 11/1998 Blickenstaff .......... G06F 3/0647
6,989,836 B2    1/2006 Ramsey
(Continued)

FOREIGN PATENT DOCUMENTS

CN    1758286 A    4/2006
CN    1805354 A    7/2006
(Continued)

OTHER PUBLICATIONS

First Office Action in Chinese Application No. 201610541853.5 dated Jul. 27, 2018, 20 pages.
(Continued)

*Primary Examiner* — Phi Hoang
(74) *Attorney, Agent, or Firm* — Metis IP LLC

(57) ABSTRACT

The present disclosure discloses a method for image rendering. The method may include obtaining first image data by a first processing device; performing a first rendering operation on the first image data; and determining second image data based on the first image data. The method may further include receiving a non-rendering operation on the second image data by the second processing device; and performing a second rendering operation on the non-rendered second image data.

11 Claims, 11 Drawing Sheets

Related U.S. Application Data continuation of application No. PCT/CN2016/112153, filed on Dec. 26, 2016.

(51) Int. Cl.

| | | |
|---|---|---|
| *G06T 19/00* | (2011.01) | |
| *G16H 30/40* | (2018.01) | |
| *G16H 30/20* | (2018.01) | |
| *G06T 7/38* | (2017.01) | |
| *G06T 11/00* | (2006.01) | |
| *G06F 17/10* | (2006.01) | |
| *G06T 7/00* | (2017.01) | |

(52) U.S. Cl.
CPC ............. *G06T 19/00* (2013.01); *G16H 30/20* (2018.01); *G16H 30/40* (2018.01); *G06F 17/10* (2013.01); *G06T 7/0012* (2013.01)

(58) Field of Classification Search
CPC ....... G06T 11/40; G06T 7/0012; G16H 30/20; G16H 30/40
See application file for complete search history.

(56) References Cited

U.S. PATENT DOCUMENTS

| | | | |
|---|---|---|---|
| 2002/0104097 A1* | 8/2002 | Jerding | ............ H04L 69/24 |
| | | | 725/115 |
| 2005/0027823 A1 | 2/2005 | Rana | |
| 2006/0136446 A1* | 6/2006 | Hughes | ............ G06F 16/10 |
| 2006/0152636 A1 | 7/2006 | Matsukawa et al. | |
| 2006/0262994 A1 | 11/2006 | Patera et al. | |
| 2007/0046966 A1 | 3/2007 | Mussack et al. | |
| 2007/0269117 A1 | 11/2007 | Ernvik et al. | |
| 2008/0101182 A1 | 5/2008 | Chikaoka et al. | |
| 2009/0016641 A1 | 1/2009 | Paladini et al. | |
| 2009/0193182 A1 | 7/2009 | Nitta | |
| 2009/0201303 A1 | 8/2009 | Westerhoff et al. | |
| 2009/0231466 A1* | 9/2009 | Morgan | ............ H04N 5/772 |
| | | | 348/231.1 |
| 2012/0198134 A1 | 8/2012 | Nakashita | |
| 2013/0268738 A1* | 10/2013 | Zhang | ............ G06F 3/0619 |
| | | | 711/162 |
| 2013/0305138 A1 | 11/2013 | Gicovate | |
| 2014/0035900 A1 | 2/2014 | Edward, III et al. | |
| 2014/0074913 A1 | 3/2014 | Claydon | |
| 2014/0143651 A1 | 5/2014 | Klotzer | |
| 2014/0195640 A1* | 7/2014 | Kaiser | ............ G06F 16/273 |
| | | | 709/217 |
| 2014/0329568 A1* | 11/2014 | Xue | ............ G10K 11/16 |
| | | | 455/570 |
| 2015/0313578 A1 | 11/2015 | Yu et al. | |
| 2016/0364902 A1 | 12/2016 | Hong et al. | |
| 2017/0091939 A1 | 3/2017 | Kluckner et al. | |
| 2018/0121101 A1* | 5/2018 | Thind | ............ G06F 3/0605 |

FOREIGN PATENT DOCUMENTS

| | | |
|---|---|---|
| CN | 1845177 A | 10/2006 |
| CN | 101976458 A | 2/2011 |
| CN | 102857791 A | 1/2013 |
| CN | 103167222 A | 6/2013 |
| CN | 103247067 A | 8/2013 |
| CN | 103440207 A | 12/2013 |
| CN | 104052803 A | 9/2014 |
| CN | 104461788 A | 3/2015 |
| CN | 104796393 A | 7/2015 |
| CN | 104881890 A | 9/2015 |
| CN | 104994333 A | 10/2015 |
| CN | 105488837 A | 4/2016 |
| CN | 106202927 A | 12/2016 |
| JP | 2003085008 A | 3/2003 |
| WO | 2011051103 A1 | 5/2011 |

OTHER PUBLICATIONS

Zheng Liping et al., Remote Visualization Based on Distributed Rendering Framework, Journal of Computer Research and Development, 49(7): 1438-1447, 2012.

Jin Ping et al., Remote-rendering Based 3D Model Publishing System, Journal of Beijing University of Aeronautics and Astronautics, 32(3): 337-341, 2006.

International Search Report in PCT/CN2016/112153 dated Mar. 2, 2017, 7 pages.

* cited by examiner

SYSTEMS AND METHODS FOR DATA DELETION

CROSS-REFERENCE TO RELATED APPLICATIONS

This application is a continuation of U.S. application Ser. No. 15/638,600, filed on Jun. 30, 2017, which is a continuation of International Application No. PCT/CN2016/112153, filed on Dec. 26, 2016, which claims priority to Chinese Application No. 201511022787.2, filed on Dec. 30, 2015, and Chinese Application No. 201610541853.5, filed on Jul. 11, 2016, the contents of which are incorporated herein by reference.

TECHNICAL FIELD

The present disclosure generally relates to a method for data processing, and in particular, a system and method for rendering and deleting medical image data.

BACKGROUND

With the development of medical imaging technology and computer technology, imaging techniques and devices such as X-ray imaging, Computerized Tomographic (CT), Magnetic Resonance Imaging (MRI), Ultrasound Imaging (US) and Positron Emission Tomography (PET) are playing an important role in clinical and research work in medical institutions. Meanwhile, medical image data generated by the medical imaging devices become more and more.

On one hand, the rendering of the medical image data requires high-performance graphics and uses much memory. In this situation, the result of a user's display-related operation is usually obtained from rendering by a remote processing device. If the result is not returned timely because of the load of the remote processing device, network, or other reasons, the user may feel that the display is not smooth, which may affect the viewing experience. Therefore, there is a need for a method that may smoothly display the user's operation and the rendered image data at a local processing device.

On the other hand, the medical image data may take up a lot of storage space. If the storage is not cleaned up in time, in the next scan, there may be cases in which the scanning may not be performed due to insufficient storage space.

SUMMARY

According to some embodiments of the present disclosure, a method is provided. The method may include obtaining first image data by a first processing device; performing a first rendering operation on the first image data; and determining second image data based on the first image data. The method may further include receiving a non-rendering operation on the second image data; and performing a second rendering operation on the non-rendered second image data.

In some embodiments, the method may further include obtaining the second image data by pre-processing the first image data.

In some embodiments, the pre-processing operation may include a downsampling operation or a compression operation.

In some embodiments, the first processing device may be a remote device and the second processing device may be a local device.

In some embodiments, the method may further include performing, by the first processing device, a third rendering operation on the first image data, wherein the third rendering operation may be based on one more non-rendering operations.

In some embodiments, the non-rendering operation may include rotation, zooming, panning, or window adjustment.

In some embodiments, the first image data may be medical image data.

In some embodiments, the first rendering operation may be a volume rendering operation.

In some embodiments, the method may further include executing, by a browser of the second processing device, the second rendering operation.

In some embodiments, the browser may execute the second rendering operation by a Web Graphics Library (WEBGL) technology.

In some embodiments, the method may further include obtaining a graphic processing capability of the second processing device.

In some embodiments, the second image data may relate to the graphic processing capability of the second processing device.

According to some other embodiments of the present disclosure, a method is provided. The method may include comparing remaining storage capacity of a storage device with a first threshold; obtaining a first determination result based on determining that the remaining storage capacity is less than the first threshold; and performing a first deletion operation based on the first determination result. The first deletion operation may include ranking a plurality of stored contents in the storage device based on last use time and number of uses; determining a first stored content to be deleted based on the ranking; and deleting the first stored content.

In some embodiments, the method may include obtaining a second determination result based on determining that the remaining storage capacity is less than the first threshold after performing the first deletion operation; and performing a second deletion operation based on the second determination result. The second deletion operation may include ranking remaining stored contents of the plurality of stored contents in the storage device based on last use time and the ratio of storage time to number of uses; determining a second stored content to be deleted based on the ranking; and deleting the second stored content.

In some embodiments, the method may further include obtaining a third determination result based on determining that the ratio of storage time to number of uses is equal to or less than a second threshold; and replacing the first threshold by a current remaining storage capacity based on the third determination result.

In some embodiments, the method may further include obtaining a fourth determination result based on determining that the remaining storage capacity is still less than the first threshold after performing the first deletion operation and the second deletion operation; and performing a third deletion operation based on the fourth determination result. The third deletion operation may include ranking remaining stored contents of the plurality of stored contents in the storage device based on last use time and number of uses; determining a third stored content to be deleted based on the ranking; and deleting the third stored content.

In some embodiments, the method may further include obtaining a fifth determination result based on determining that the first threshold is an invalid threshold; and setting a new first threshold based on the fifth determination result.

In some embodiments, the method may further include obtaining a sixth determination result based on determining that a plurality of stored contents to be deleted has the same ranking in the first deletion operation or the second deletion operation; and performing a fourth deletion operation for deleting stored contents to be deleted based on the sixth determination result.

In some embodiments, the fourth deletion operation may include ranking the stored contents to be deleted based on last use time, storage time, number of uses, size, type, name, or the like, or any combination thereof; determining a fourth stored content to be deleted based on the ranking; and deleting the fourth stored content.

In some embodiments, the method may further include obtaining a seventh determination result based on determining that a plurality of stored contents to be deleted has the same ranking in the first deletion operation or the second deletion operation; and simultaneously deleting the plurality of stored contents with the same ranking based on the seventh determination result.

According to some other embodiments of the present disclosure, a non-transitory computer readable medium is provided. The medium may include executable instructions that, when executed by at least one processor, cause the at least one processor to effectuate a method. The method may include obtaining first image data by a first processing device; performing a first rendering operation on the first image data; determining second image data based on the first image data; receiving a non-rendering operation on the second image data by a second processing device; and performing a second rendering operation on the non-rendered second image data.

According to some other embodiments of the present disclosure, a non-transitory computer readable medium is provided. The medium may include executable instructions that, when executed by at least one processor, cause the at least one processor to effectuate a method. The method may include comparing a remaining storage capacity of a storage device with a first threshold; obtaining a first determination result based on determining that the remaining storage capacity is less than the first threshold; and performing a first deletion operation based on the first determination result. The first deletion operation may include ranking a plurality of stored contents in the storage device based on last use time and number of uses; determining a first stored content to be deleted based on the ranking; and deleting the first stored content.

According to some other embodiments of the present disclosure, a system is provided. The system may include at least one processor and information. The information that, when executed by the at least one processor, cause the at least one processor to: obtain first image data by a first processing device; perform a first rendering operation on the first image data; and determine second image data based on the first image data; and receive a non-rendering operation on the second image data by a second processing device; and perform a second rendering operation on the non-rendered second image data.

According to some other embodiments of the present disclosure, a system is provided. The system may include at least one processor and information. The information that, when executed by the at least one processor, cause the at least one processor to: compare a remaining storage capacity of a storage device with a first threshold; obtain a first determination result based on determining that the remaining storage capacity is less than the first threshold; and perform a first deletion operation based on the first determination result. The first deletion operation may include ranking a plurality of stored contents in the storage device based on last use time and number of uses; determine a first stored content to be deleted based on the ranking; and delete the first stored content.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

DETAILED DESCRIPTION

As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

Some modules of the system may be referred to in various ways according to some embodiments of the present disclosure. However, any number of different modules may be used and operated in a client terminal and/or a server. These modules are intended to be illustrative, and not intended to limit the scope of the present disclosure. Different modules may be used in different aspects of the system and method.

According to some embodiments of the present disclosure, flowcharts are used to illustrate the operations performed by the system. It is to be expressly understood, the operations above or below may or may not be implemented in order. Conversely, the operations may be performed in inverted order, or simultaneously. Besides, one or more other operations may be added to the flowchart, or one or more operations may be omitted from the flowchart.

Figure 1:
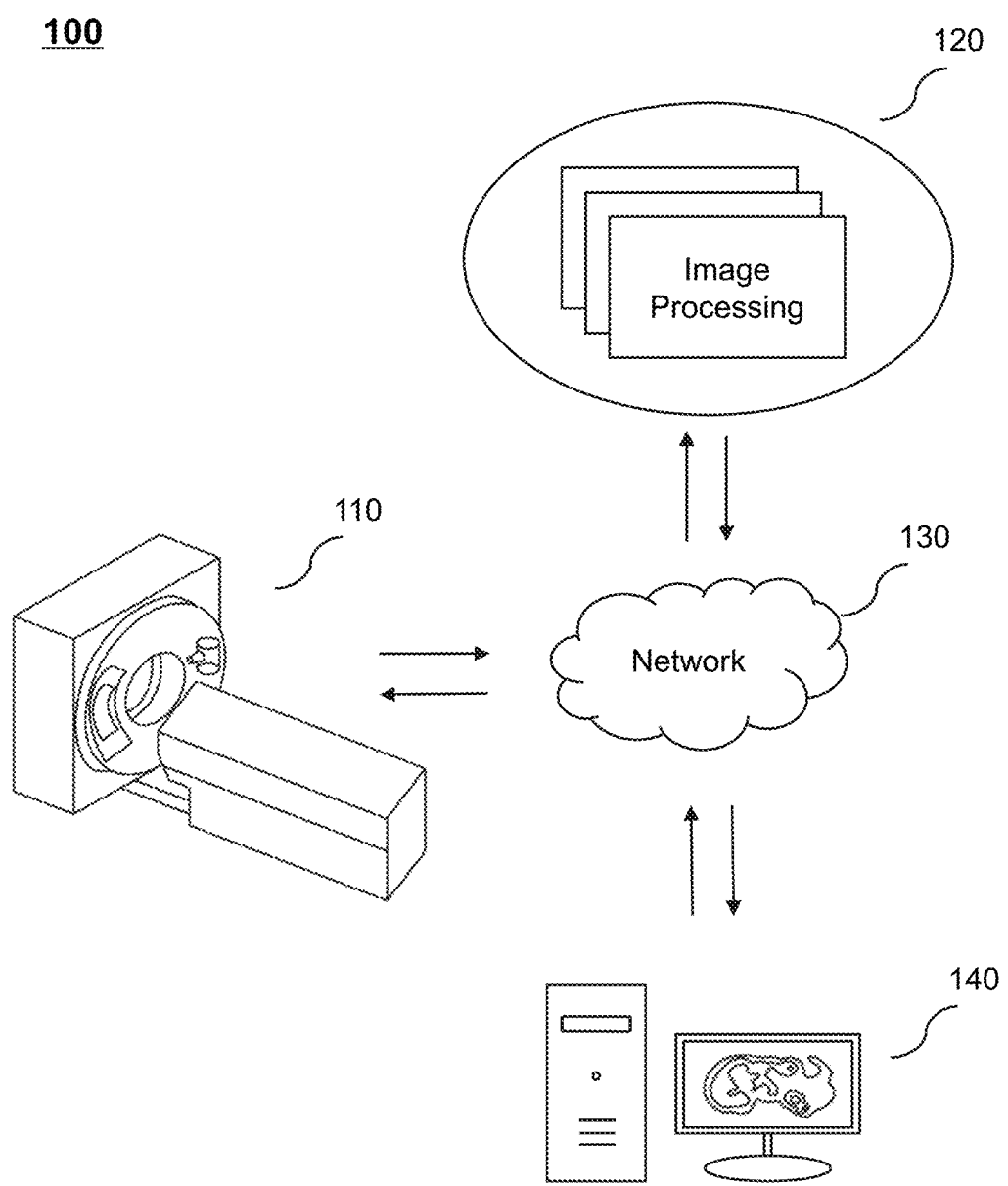
FIG. 1 is an application scenario diagram of an imaging system according to some embodiments of the present disclosure.

FIG. 1 is an application scenario diagram of an imaging system according to some embodiments of the present disclosure. The imaging system 100 may include an imaging device 110, a remote processing device 120, and a local processing device 140. The imaging device 110, the remote processing device 120, and the local processing device 140 may communicate with each other via a network 130.

The imaging device 110 may scan a target. In some embodiments, the imaging device 110 may be a medical imaging device. The medical imaging device may collect information of various parts of a patient's body. In some embodiments, the imaging device 110 may be a magnetic resonance imaging (MRI), a computed tomography (CT), a positron emission computed tomography (PET), a b-scan ultrasonography, thermal texture maps (TTM), or a medical electronic endoscope (MEE), etc. Further, image data obtained by the imaging device 110 may be transmitted to the remote processing device 120 or the local processing device 140 via the network 130.

The remote processing device 120 may store and process obtained image data. The remote processing device 120 may be a file server, a database server, a network storage server, a specifically designed server with special functions, etc. In some embodiments, the remote processing device 120 may be a Picture Archiving and Communication System (PACS). In some embodiments, the remote processing device 120 may perform on the image data a pre-processing operation, an image rendering operation, a post-processing operation, etc., and transmit a processing result to the local processing device 140. In some embodiments, objects to be processed may be image files generated according to Digital Imaging and Communications in Medicine (DICOM) protocol or other types of DICOM files. It should be noted that the DICOM files, DICOM data, and related service communication may all refer to image files, files of post-processing, and other types of files generated by other related operations or processes, all of which are constructed according to the Digital Imaging and Communications in Medicine (DICOM) protocol, and communications and post-processing services constructed according to the protocol.

The local processing device 140 may present processed image data to a user. In some embodiments, the local processing device 140 may transmit a request for loading an image to the remote processing device 120. In some embodiments, the local processing device 140 may perform an image processing (e.g., a rendering operation) on the image data that has a relatively low sampling rate or that has been compressed. In some embodiments, the local processing device 140 may be a local server, a workstation, a computer, a tablet computer, a laptop, etc. In some embodiments, the local processing device 140 may display and process the image data via a browser. In some embodiments, the local processing device 140 may receive an input or an operation from a user.

The network 130 may be used for internal communication of the imaging system 100, receiving information outside the system, transmitting information to the outside of the system, etc. In some embodiments, the imaging device 110, the remote processing device 120, and the local processing device 140 may access the network 130 via a wired connection, a wireless connection, or a combination of both. The network 130 may be a single network or a combination of multiple networks. In some embodiments, the network 130 may include a local area network, a wide area network, a public network, a private network, a wireless local area network, a virtual network, a metropolitan area network, a public switched telephone network, or the like, or any combination thereof. In some embodiments, the network 130 may include a variety of network access points, such as wired or wireless access points, base stations, or network switching points, etc. Via an access point, a data source may be connected to the network 130 and transmit information via the network 130.

In some embodiments, the imaging device 110 and the local processing device 140 may be local devices, and the remote processing device 120 may be a remote device. Further, the local processing device 140 may control the imaging device 110 to obtain image data of a scanning target and transmit it to the remote processing device 120 via the network 130 to be stored and processed. In some embodiments, the remote processing device 120 may be connected to a plurality of local processing devices 140.

Figure 2A:
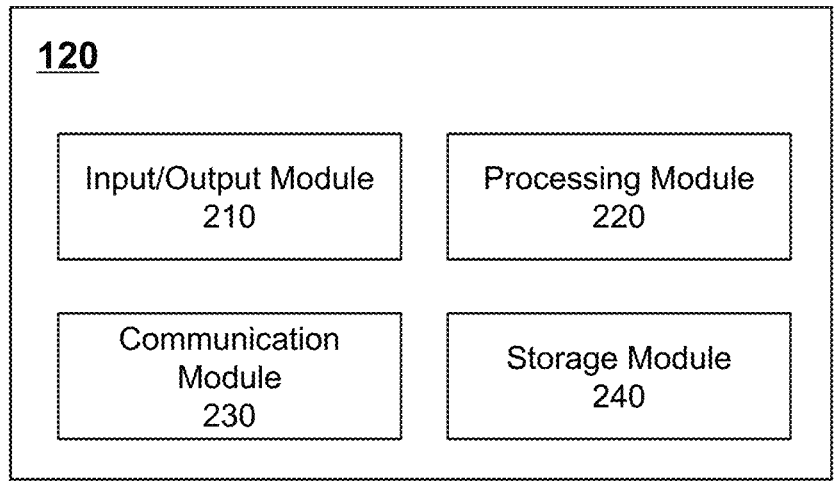
FIG. 2A is a schematic block diagram of a remote processing device according to some embodiments of the present disclosure.

FIG. 2A is a schematic block diagram of a remote processing device according to some embodiments of the present disclosure. The remote processing device 120 may include an input/output module 210, a processing module 220, a communication module 230, and a storage module 240. The connection among the modules of the remote processing device 120 may be a wired connection, a wireless connection, or a combination of both. The corresponding relationships among the modules may be one-to-one or one-to-many. For example, the remote processing device 120 may include a plurality of input/output modules 210 and one processing module 220. The plurality of input/output modules 210 may respectively receive requests for data inputting and image processing from a plurality of local processing devices 140, and transmit the requests to the processing module 220 to be processed. As another example, the remote processing device 120 may include a plurality of input/output modules 210 and a plurality of processing modules 220. Each processing module 220 may correspond to an input/output module 210 and process the data input by the corresponding input/output module 210 respectively. Parameters may be configured by presetting the input/output module 210, which may include storage time, deletion order, etc.

The input/output module 210 may receive information from other modules in the system 100 or external modules outside the system 100. The input/output module 210 may also transmit information to other modules in the system 100 or external modules outside the system 100. In some embodiments, the input/output module 210 may receive image data generated by the imaging device 110 or an image processing request according to operation instructions from a user transmitted by the local processing device 140, etc. The image data may include X-ray image data, magnetic resonance image data, ultrasonic image data, thermal image data, nuclear image data, optical image data, etc. Methods for obtaining the image data may be found elsewhere in the present disclosure, for example, FIG. 6 and the description thereof. In some embodiments, the operation instructions from a user may include instructions for performing operations on the image data or images corresponding to the image data, such as rotation, zooming, panning, window adjustment, etc. In some embodiments, information received by the input/output module 210 may include information in the form of digital, text, image, sound, video, etc. In some embodiments, the received information may be processed by the processing module 220 or stored in the storage module 240.

In some embodiments, the input/output module 210 may receive configuration information of one or more local processing devices 140. The configuration information may include an image processing capability of the local processing device 140, a CPU load of the local processing device 140, etc.

In some embodiments, the input/output module 210 may output a processing result of the image data. The processing result may be pre-processed image data, or rendered images, etc. In some embodiments, the processing result may be transmitted to one or more local processing devices 140 via the network 130. The processing result output by the input/output module 210 may include a result in the form of digital, text, image, video, or the like, or other special prescribed forms. In some embodiments, the data received and/or output by the input/output module 210 may be data or files constructed by Digital Imaging and Communications in Medicine (DICOM). Data with the DICOM protocol format may be stored and transmitted according to a particular standard or a DICOM communication standard.

The processing module 220 may be configured to process image data. In some embodiments, the processing module 220 may obtain the image data from the imaging device 110 via the input and output module 210. In some embodiments, the processing module 220 may obtain the image data from the storage module 250. In some embodiments, the processing module 220 may perform processing on the obtained image data. The processing may include high-pass filtering, Fourier transform, fitting, interpolation, discrete, bulk ray projection, texture mapping, radiation coloring, ray tracing, ray premature termination, octree, pseudo-color enhancement, grayscale window, model Base coding, neural network coding, region-based segmentation, etc. In some embodiments, the processing module 220 may pre-process medical data. The pre-processing may include downsampling, or data compression, etc. In some embodiments, the processing module 220 may perform further processing on generated results. The further processing may include image processing, such as image enhancement, image reconstruction, image segmentation, image recognition, etc.

In some embodiments, the processing module 220 may obtain image operation instructions via the local processing device 140. According to the image operation instructions, the processing module 220 may perform operations on the image data in the coordinate space, such as rotation, panning, zooming, mirroring, multi-planar reconstruction, window width, and window position adjustment, etc. For example, the processing module 220 may perform a multi-planar reconstruction on a transverse axis image to obtain two-dimensional images of a coronal plane, a sagittal plane, a horizontal axis, and a bevel plane. In some embodiments, the processing module 220 may calculate spatial coordinates, angles, geometries, coloring, etc. of the three-dimensional image processed by the above-described operations. For example, the processing module 220 may obtain the RGB value or the greyscale value of each pixel of the image data that is window width and/or window position adjusted.

In some embodiments, the processing module 220 may be one or more processing components or devices, such as a central processing unit (CPU), a graphics processing unit (GPU), a digital signal processor (DSP), a system on a chip (SoC), a microcontroller unit (MCU), etc. In some embodiments, the processing module 220 may also be a specially designed processing component or device with special functions.

The communication module 230 may establish communication between the remote processing device 120 and the network 130. The communication mode may include a wired communication and wireless communication. The wired communication may be a communication implemented via a transmission medium including wire, a cable, an optical cable, a waveguide, a nanomaterial, etc. The wireless communication may include IEEE 802.11 series wireless local area network communication, IEEE 802.15 series wireless communication (e.g., Bluetooth, ZigBee), mobile communication (e.g. CDMA, WCDMA, TD-SCDMA, TD-LTE, FDD-LTE), satellite communication, microwave communication, scattering communication, or atmospheric laser communication, etc. In some embodiments, the communication module 230 may encode transmitted information according to one or more encoding methods. The one or more encoding methods may include phase coding, non-zero coding, or differential Manchester coding, etc. In some embodiments, the communication module 230 may select different encoding methods and transmission modes based on types of data or processed images. For example, when the image data or the processed image is constructed in accordance with the DICOM protocol, the communication module 230 may encode and transmit the image data or the processed image according to the DICOM standard. In some embodiments, the communication module 230 may include a data calibration unit for calibrating errors generated during encoding and transmission.

The storage module 240 may be configured to store information. The information may include image data and operation instructions of a user obtained by the input/output module 210, processing results generated by the processing module 220, etc. The storage module 240 may store information in a format of text, digital, sound, image, video, etc. In some embodiments, the storage module 240 may be storage devices of various types such as a solid-state hard disk, a mechanical hard disk, a USB flash memory, an SD memory card, an optical disk, a random-access memory (RAM), a read-only memory (ROM), etc. In some embodiments, the storage module 240 may be one or more mass storages, for example, a mass storage array managed by one or more controllers. In some embodiments, the storage module 240 may be a local storage of the remote processing device 120, external storage, storage (e.g., a cloud storage) that is communicatively connected via the network 130, etc. In some embodiments, the storage module 240 may include a data management unit. The data management unit may monitor and manage stored contents in the storage module 240, delete data with zero or relatively low utilization, and ensure that the storage module includes sufficient storage capacity on the premise that the current user can perform operations normally.

It should be noted that the above description of the modules in the remote processing device 120 merely provides some specific embodiments, and should not be considered as the only practical solution. It will be apparent to those skilled in the art that, after understanding the basic principle of the modules, various modifications and changes to the configuration of the remote processing device may be made without departing from the principle. However, these modifications and changes are still within the scope of the present disclosure.

For example, the remote processing device 120 may include a control module configured to control each module of the remote processing device 120 for receiving, storing, processing, outputting image data, etc. For example, the input/output module 210 may obtain information (e.g., system upgrades, expert advice) from the network 130, or output information to the network 130 (e.g., sharing patient information in a healthcare system).

Figure 2B:
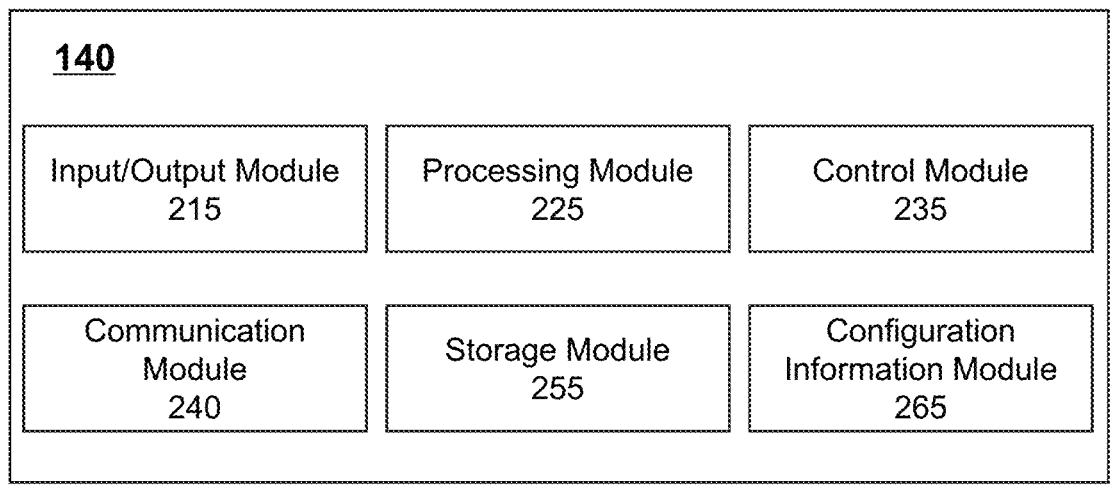
FIG. 2B is a schematic block diagram of a local processing device according to some embodiments of the present disclosure.

FIG. 2B is a block diagram of a local processing device according to some embodiments of the present disclosure. The local processing device 140 may include an input/output module 215, a processing module 225, a control module 235, a communication module 245, a storage module 255, and a configuration information module 265. The connection among the modules of the local processing device 120 may be a wired connection, a wireless connection, or a combination of both. The corresponding relationships among the modules may be one-to-one or one-to-many. For example, the local processing device 140 may include a plurality of input/output modules 215 and a processing module 225. The plurality of input/output modules 215 may respectively receive requests for data inputting and image processing from a plurality of remote processing devices 120, and transmit the requests to the processing module 225 to be processed. As another example, the local processing device 140 may include a plurality of input/output modules 215 and a plurality of processing modules 225. Each processing module 225 may correspond to an input/output module 215, and then process the data input by the corresponding input/output module 215, respectively.

The input/output module 215 may receive information from other modules in the system 100 or external modules outside the system 100. The input/output module 215 may also transmit information to other modules in the system 100 or external modules outside the system 100. In some embodiments, the input/output module 215 may receive image data generated by the imaging device 110. The image data may include X-ray image data, magnetic resonance image data, ultrasonic image data, thermal image data, nuclear image data, or optical image data, etc. In some embodiments, the input/output module 215 may receive information generated by the remote processing device 120. The information may include image data, processed images, etc. In some embodiments, the image data may be image data pre-processed by data compression, downsampling, etc. In some embodiments, the processed images may be images processed by image rendering, image enhancement processing, image segmentation, image coding, image reconstruction, etc.

In some embodiments, the input/output module 215 may receive information input by a user. The manner in which the user may input the information may include a mouse operation, a keyboard operation or a button operation, a handwriting operation, a touch screen operation, a gesture operation, etc. For example, the input/output module 215 may receive clicks and drags of the mouse for performing operations on images in the local processing device 140, such as panning, rotation, zooming, etc. For example, the input/output module 215 may receive basic information input by the user, such as patient name, medical history, etc. In some embodiments, the information input by the input/output module 215 may be saved to the storage module 255 or transmitted to the processing module 225 to be processed.

In some embodiments, the local processing device 140 may output information to the remote processing device 120 or to a user via the input/output module 215. The information output from the input/output module 215 to the remote processing device 120 may include instructions for obtaining specific information in the remote processing device 120, instructions for requesting the remote processing device 120 to process data or images, operation instructions for images from a user, etc. In some embodiments, the information output from the input/output module 215 to the user may include processed images, etc. The input/output module 215 may output information to the user in a format of character, image, sound, or the like, or any combination thereof. In some embodiments, the input/output module 215 may output the information via a physical output device, such as a LED indicator, an LCD, a speaker, etc. In some embodiments, the input/output module 215 may use a virtual reality technology to output information. For example, lesion information of a patient's tissue or organ may be presented by a holographic image.

In some embodiments, via the input/output module 215, the local processing device 140 may output control information, operating parameters, etc., to the imaging device 110, which may be configured to control the operating state of the imaging device 110 or to control the imaging device 110 to collect information of a scanning object.

The processing module 225 may process image data or user's operation instructions for imaging. In some embodiments, the processing module 225 may process the image data by one or more methods. The one or more methods may include a method of wavelet transforming, filtering, texture mapping, radiation coloring, ray tracing, binary tree, histogram enhancement, grayscale window, model base coding, neural network based coding, or threshold-based segmentation, etc. In some embodiments, the image data may be obtained by a pre-process by the remote processing device 120. In some embodiments, the pre-processing may include down sampling, data compression, etc. In some embodiments, the processing module 225 may also perform statistical analysis on the image data and corresponding images and then generate a statistical result report.

In some embodiments, the processing of the image data and corresponding images may be implemented by a program or a separate component (e.g., a dedicated software, a browser, a programming of a user) of the local processing device 140. In some embodiments, the processing of the image data and corresponding images may be performed by a browser of the local processing device 140. In some embodiments, the browser may implement the process using a Web Graphics Library (WEBGL) technology.

In some embodiments, the processing module 225 may process image operation instructions received from a user. The user may perform one or more operations on an image via the input/output module 215. The operations may include rotation, panning, mirroring, window adjustment, phase reversing, etc. In some embodiments, the processing module 225 may process the operation(s) performed by the user on the image. The processing module 225 may convert the operation(s) into a format that is easy to calculate or process, such as a conversion matrix, a vector, a table, etc. In some embodiments, the processing module 225 may convert the user's operation performed on the image into a conversion matrix. In some embodiments, the processing module 225 may combine the conversion matrices corresponding to multiple operations to generate a composite conversion matrix, as shown in the following Formula (1):

$$\begin{bmatrix} m_{00} & m_{10} & m_{20} & m_{30} \\ m_{01} & m_{11} & m_{21} & m_{31} \\ m_{02} & m_{12} & m_{22} & m_{32} \\ m_{03} & m_{13} & m_{23} & m_{33} \end{bmatrix}, \quad (1)$$

where the vector sum of a parallel projection (, , ,) may be either 1 or 0. The corresponding panning vector may be (, ,). The zooming coefficients of the corresponding x, y, and z may be expressed as Formula (2), Formula (3) and Formula (4), respectively:

$$\text{Zoom}_x = \sqrt{(m_{00}^2 + m_{01}^2 + m_{02}^2)} \quad (2)$$

$$\text{Zoom}_y = \sqrt{(m_{10}^2 + m_{11}^2 + m_{12}^2)} \quad (3)$$

and $$\text{Zoom}_z = \sqrt{(m_{20}^2 + m_{21}^2 + m_{22}^2)} \quad (4)$$

The corresponding rotation matrix may be expressed by Formula (5):

$$\begin{bmatrix} \frac{m_{00}}{\text{Zoom}_x} & \frac{m_{10}}{\text{Zoom}_y} & \frac{m_{20}}{\text{Zoom}_z} & 0 \\ \frac{m_{01}}{\text{Zoom}_x} & \frac{m_{11}}{\text{Zoom}_y} & \frac{m_{21}}{\text{Zoom}_z} & 0 \\ \frac{m_{02}}{\text{Zoom}_x} & \frac{m_{12}}{\text{Zoom}_y} & \frac{m_{22}}{\text{Zoom}_z} & 0 \\ 0 & 0 & 0 & 1 \end{bmatrix}. \quad (5)$$

The control module 235 may generate control information. In some embodiments, the control module 235 may control the imaging device 110 to scan a scanning target, control the remote processing device 120 to perform a data processing, control the local processing device 140 to output displaying, etc. For example, the control module 235 may control the imaging device 110 to collect image data in accordance with a preset parameter via a work program customized for diseases or anatomical sites. For example, the control module 235 may control the imaging device 110 to transmit the image data to the remote processing device 120 for image processing and return to the local processing device 140 for output display. For example, according to a user's needs, the control module 235 may record the image data associated with the user and corresponding operations and processes at a corresponding part of the remote processing device 120.

The communication module 245 may establish communication between the local processing device 140 and the network 130. The communication module 245 may transmit information by a wired connection or a wireless connection. In some embodiments, the communication module 245 may encode the transmitted information using one or more encoding methods. In some embodiments, the communication module 245 may have a function or a form similar to the communication module 230.

The storage module 255 may be configured to store information. The information that the storage module 255 may store may include information (e.g., image data, images, information input by a user) obtained by the input/output module 215, processing results generated by the processing module 225, control instructions generated by the control module 235, etc. The storage module 255 may use one or more storage media that may be read or written, including a static random access memory (SRAM), a random-access memory (RAM), a read-only memory (read-Only memory, ROM), a hard disk, a flash memory, etc.

The configuration information module 265 may obtain configuration information of the imaging system 100. The configuration information may include parameter information of the system, such as hardware, software, network, etc. In some embodiments, the configuration information obtained by the configuration module 265 may include a type, a probe model, an operating parameter of the imaging device 110, a type and a storage capacity of the remote processing device 120, a type of the processing module 220, a type of the local processing device 140, a model of the processing module 225, graphics processing speed, a bandwidth and a delay of the network 130, etc. In some embodiments, according to configuration information of the local processing device 140 and the network 130 obtained by the configuration information module 265, the remote processing device 120 may determine a degree of a pre-processing operation. In some embodiments, the user may view information provided by the configuration information module 265 and determine whether the entire image rendering operation is performed by the remote processing device 120.

Figure 3:
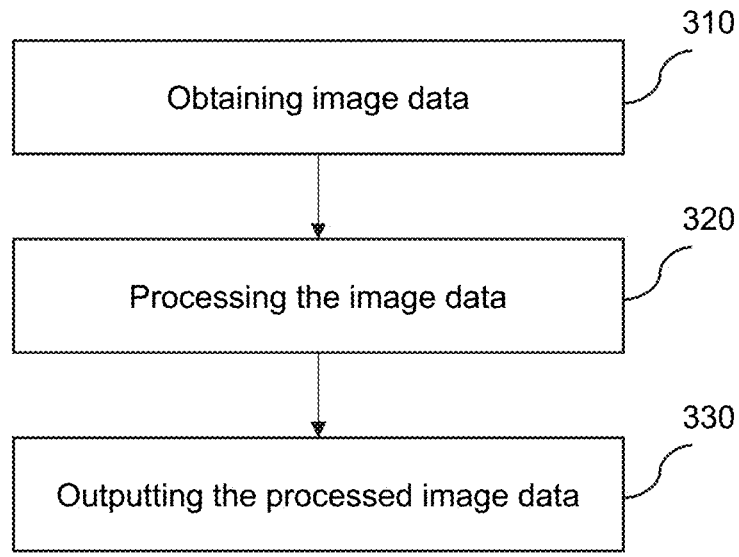
FIG. 3 is a flowchart illustrating an exemplary process of the imaging system according to some embodiments of the present disclosure.

FIG. 3 is a flowchart illustrating an exemplary process of the imaging system according to some embodiments of the present disclosure. The process 300 may be performed by the remote processing device 120 and/or the local processing device 140.

Step 310 may include obtaining image data. In some embodiments, step 310 may be performed by the input/output module 210 or the input/output module 215. In some embodiments, the image data may be obtained from the imaging device 110 by scanning a target object. In some embodiments, the image data may be obtained from an internal storage device, such as the storage module 240, the storage module 255, etc. The image data may also be obtained from an external storage device, such as a network storage device, a cloud disk, a mobile hard disk, etc. The image data may include image matrices, image information, image vectors, bitmaps, animations, image codes, image elements, image sections, or the like, or any combination thereof.

In some embodiments, the image data may be medical image data. Further, the medical image data may be obtained from one or more types of medical scans. The medical scan may include magnetic resonance imaging (MRI), X-ray computed tomography (X-ray-CT), positron computer tomography (PET), single photon emission computed tomography (SPECT), etc. In some embodiments, the image data may be obtained from a scan of one or more targets, such as an organ, a body, an object, a dysfunction, a tumor, etc. In some embodiments, the image data may be obtained from a scan of one or more targets, such as a head, a chest, an organ, a bone, a blood vessel, etc.

In some embodiments, the image data may be two-dimensional (2D) data or three-dimensional (3D) data. In some embodiments, the image data may comprise a plurality of 2D pixels or 3D voxels. Each of the values of the image data may correspond to one or more properties of each pixel or voxel, for example, grayscale, brightness, color, absorbance to X-rays or gamma rays, hydrogen atom density, etc.

Step 320 may include processing image data. The processing may include performing a non-rendering operation and a rendering operation on the image data. The rendering operation may include generating a rendering result based on the image data. In some embodiments, the rendering operation may include rendering and rasterization on a scanning line, ray projection, radiation coloring, ray tracing, skipped free space, light early termination, octree, etc. The rendering operation may be based on a feature of a scanning target, including a geometrical feature, a texture feature, a background signal feature, a background brightness, a background shadow, etc. For example, the rendering operation may include generating a rendering result based on a patient's physical characteristics, ambient light intensity, light source location, texture features, viewing angle, etc. The rendering result may be a 2D image or 3D image. In some embodiments, the rendering result may be an image that simulates a patient observed in a particular environment, a particular viewing angle, and a particular posture. In some embodiments, the rendering result may be a surface image of the scanning target. In some embodiments, a first rendering result may be the scanning target's cross-sectional image, internal image, etc.

The non-rendering operation may include compression, down sampling, rotation, panning, zooming, mirroring, multi-planar reconstruction, window width and window position adjustment, histogram enhancement, pseudo color enhancement, grayscale window, Fourier back projection method, convolution back projection method, region-based segmentation, statistic-based segmentation, etc.

Step 330 may include outputting one or more sets of processed image data. In some embodiments, the output of the image data may include transmitting the processed image data to other modules of the system. For example, in step 330, the remote processing device 120 may transmit the processed image data to the local processing device 140 via the network 130. The local processing device 140 may also transmit the processed image data to the remote processing device 120 via the network in step 330. In some embodiments, step 330 may include storing the processed image data into the storage module 240 or the storage module 255. In some embodiments, the output of the image data may include displaying the processed image data via a display component of the input/output module 210 or the input/output module 215.

In some embodiments, step 330 may include transmitting the processed image data to a module or a device outside the system. The transmission of the image data may be wireless or wired, or a combination of both. For example, the processed image data may be wirelessly transmitted to a module or a device outside the system via the communication module 230 or the communication module 245.

Figure 4:
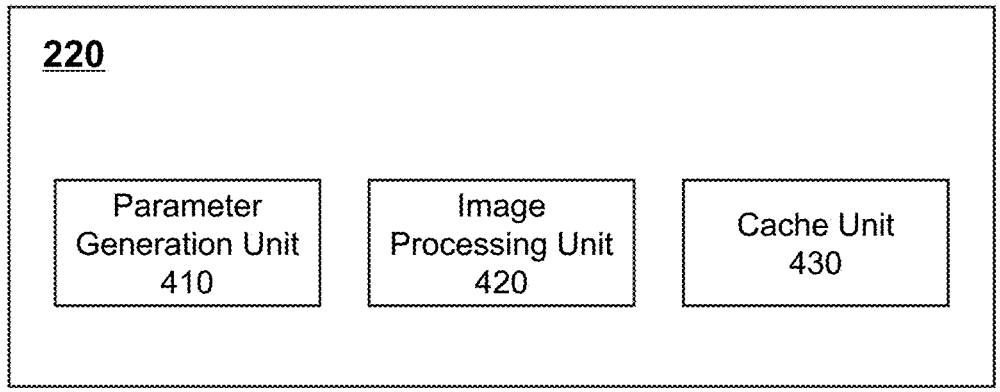
FIG. 4 is a schematic block diagram of a processing module 220 according to some embodiments of the present disclosure.

FIG. 4 is a schematic block diagram of a processing module 220 according to some embodiments of the present disclosure. The processing module 220 may include a parameter generation unit 410, an image processing unit 420, and a cache unit 430.

The parameter generation unit 410 may calculate a processing parameter of image data. According to the operation instructions from a user and the image data, the parameter generation unit 410 may generate a processing parameter of the image data. In some embodiments, the instructions of a user for performing an operation (e.g., panning, rotation, mirroring, multi-planar reconstruction (MPR), window adjustment) on the image may be converted into a composite matrix by the processing module 225. According to the composite matrix, the parameter generation unit 410 may generate an image processing parameter corresponding to the operation instructions from a user. The image processing parameter may include a scale, a contour, a coordinate, a distance, an angle, a window width, a window position, etc. In some embodiments, the processing parameter may be obtained using one or more numerical calculation methods. The numerical calculation method may include fitting, normalization, Fourier transform, integration, principal component analysis, discretization, etc.

The image processing unit 420 may process the image data obtained by the remote processing device 120. The image data may include X-ray image data, magnetic resonance image data, ultrasonic image data, thermal image data, nuclear image data, optical image data, etc. The image data received by the image processing unit 420 may be in a format of digit, graphics, image, sound, video, etc. In some embodiments, the image data may be constructed in accordance with the DICOM protocol.

The image processing unit 420 may process the received image data based on one or more methods. The one or more methods may include pre-processing, image rendering, post-processing, etc. The pre-processing may include compressing and downsampling the received medical data. The image rendering may include rendering and rasterization on a scanning line, ray projection, radiation coloring, ray tracing, skipped free space, light early termination, octree, etc. The post-processing may include histogram enhancement, pseudo color enhancement, grayscale window, Fourier back projection method, convolution back projection method, region-based segmentation, statistic-based segmentation, etc. The pre-processing, the image rendering, and the post-processing may be implemented by a method of linear algebra, calculus, numerical analysis, digital signal processing, Monte Carlo, or the like, or any combination thereof. The image processing unit 420 may process (e.g., measure, annotate) a target feature of the generated processing result. In some embodiments, according to a user's request, the image processing unit 420 may measure or mark data (e.g., length, angle, area) on the generated processing result, or make an annotation on the data. For example, according to a user's request, the image processing unit 420 may recognize a diseased region with different colors or textures on the tissue, and calculate an area or a diameter of the equivalent circle of the diseased region. In some embodiments, the image processing unit 420 may calibrate the accuracy of the processing result. In some embodiments, the calibration may be a calibration on the scanning target's geometric dimension.

The image data generated by the image processing unit 420 may be saved in one or more formats. The one or more formats may include a vector graphics format (e.g., DXG), a picture format (e.g., PNG, JPEG, BMP, GIF), a video format (e.g., MPEG, AVI, WMV), or a dedicated image format (e.g., DICOM 3.0 image format) built by DICOM protocol. In some embodiments, the image processing unit 420 may be a microprocessor, a monolithic microcomputer, a graphics processor, or a specially designed processing component or device with a particular function.

The cache unit 430 may temporarily store data. In some embodiments, the cache unit 430 may store intermediate data generated during the calculation, data with a relatively high priority, frequently used data, etc. In some embodiments, the cache unit 430 may obtain the image data to be processed by the image processing unit 420 or store information processed by the image processing unit 420. In some embodiments, the cache unit 430 may include a plurality of caches, such as an L3 cache, an L2 cache, a primary cache, etc. The cache unit 430 may be a static random access memory (SRAM), a random access memory (RAM), a read only memory (ROM), a flash memory, etc.

Figure 5:
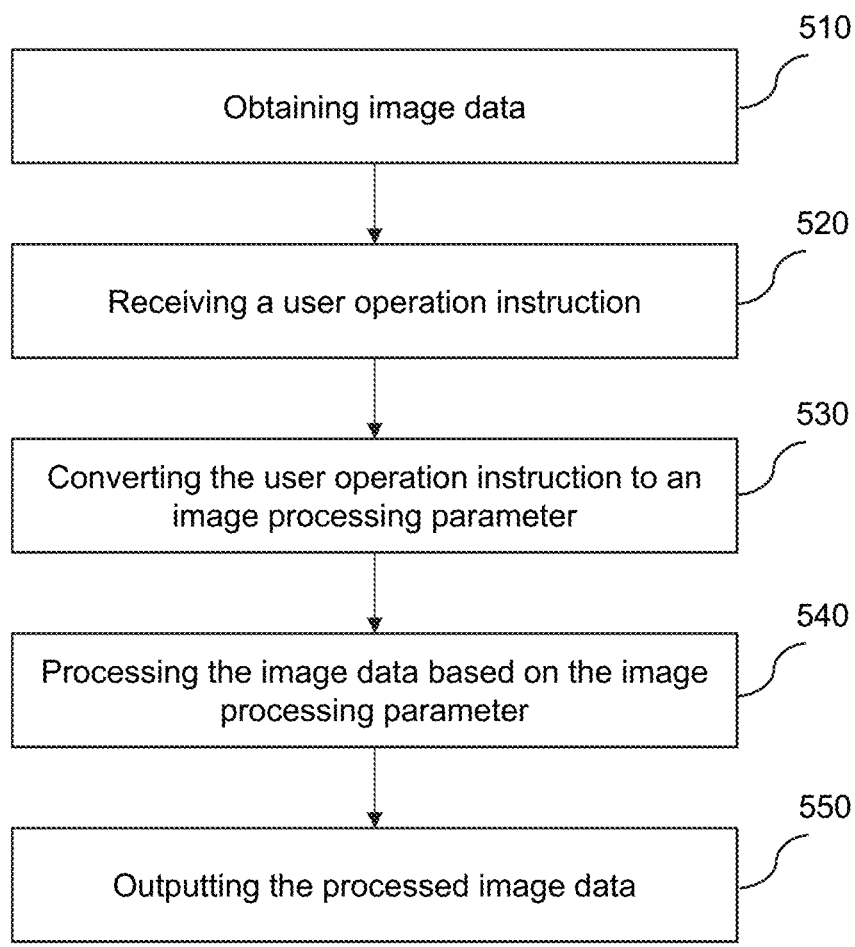
FIG. 5 is a flowchart illustrating an exemplary process for processing image data according to some embodiments of the present disclosure.

FIG. 5 is a flowchart illustrating an exemplary process for processing image data according to some embodiments of the present disclosure. In some embodiments, process 500 may be performed by the processing module 220.

Step 510 may include obtaining one or more image data. In some embodiments, the image data may be obtained according to a scan by the imaging device 110. In some embodiments, the image data may be obtained from an internal storage device (e.g., the storage module 240, the storage module 255) and/or an external storage device (e.g., a network storage device, a cloud disk, a mobile hard disk). The image data may include image matrices, image information, image vectors, bitmaps, animations, image codes, image elements, image sections, or the like, or any combination thereof.

Step 520 may include obtaining one or more operation instructions of a user. In some embodiments, the operation instruction(s) of the user may include an instruction for performing an adjustment operation (e.g., rotation, panning, zooming, mirroring, multi-planar reconstruction, window width, and window position adjustment) on the image data. In some embodiments, the operation instruction(s) of the user may be a set of instructions for continuous operations.

Step 530 may include converting one or more operation instructions of the user into image processing parameter(s). In some embodiments, step 530 may include generating an image processing parameter based on operation instructions of the user and image data. In some embodiments, the instructions of the user for performing operations (e.g., panning, rotation, mirroring, multi-planar reconstruction, window adjustment) on the image may be converted into a composite matrix. According to the composite matrix, image processing parameters corresponding to the operation instructions from the user may be generated in step 530. The image processing parameters may include a scale, a contour, a coordinate, a distance, an angle, a window width, a window position, etc. In some embodiments, the processing parameters may be obtained using one or more numerical calculation methods. The numerical calculation method may include fitting, normalization, Fourier transform, integration, principal component analysis, discretization, etc.

Step 540 may include processing the image data in accordance with the image processing parameter(s). The processing may include pre-processing, image rendering operations, post-processing, etc. The pre-processing may include compressing and downsampling the received medical data. The image rendering operation may include rendering and rasterization on a scanning line, ray projection, radiation coloring, ray tracing, skipped free space, light early termination, octree, etc. The post-processing may include histogram enhancement, pseudo color enhancement, grayscale window, Fourier back projection method, convolution back projection method, region-based segmentation, statistic-based segmentation, etc. The processing method may be implemented by a method of linear algebra, calculus, numerical analysis, digital signal processing, Monte Carlo, or the like, or any combination thereof. In some embodiments, according to a user request, data (e.g., length, angle, area) may be measured or marked according to the generated processing result, or may be annotated. For example, according to a user request, a diseased region with different colors or textures on the tissue may be recognized, and the area or the diameter of the equivalent circle of the diseased region may then be determined, etc. In some embodiments, the accuracy of the processing results may be further calibrated in step 540. In some embodiments, the calibration may be a calibration of a scanning target's geometric dimensions.

Step 550 may include outputting the processed image data. In some embodiments, the output of the image data may include transmitting the processed image data to other modules of the system. For example, in step 550, the remote processing device 120 may transmit the processed image data to the local processing device 140 via the network 130. The local processing device 140 may also transmit the processed image data to the remote processing device 120 via the network 130 in step 550. In some embodiments, step 550 may include storing the processed image data into the storage module 240 or the storage module 255. In some embodiments, the output of the image data may include displaying the processed image data via a display component of the input/output module 210 or the input/output module 215.

In some embodiments, step 550 may include transmitting the processed image data to a module or device outside the system. The transmission of the image data may be wireless, wired, or a combination of both. For example, the processed image data may be wirelessly transmitted to a module or device outside the system via the communication module 230 or the communication module 245.

Figure 6:
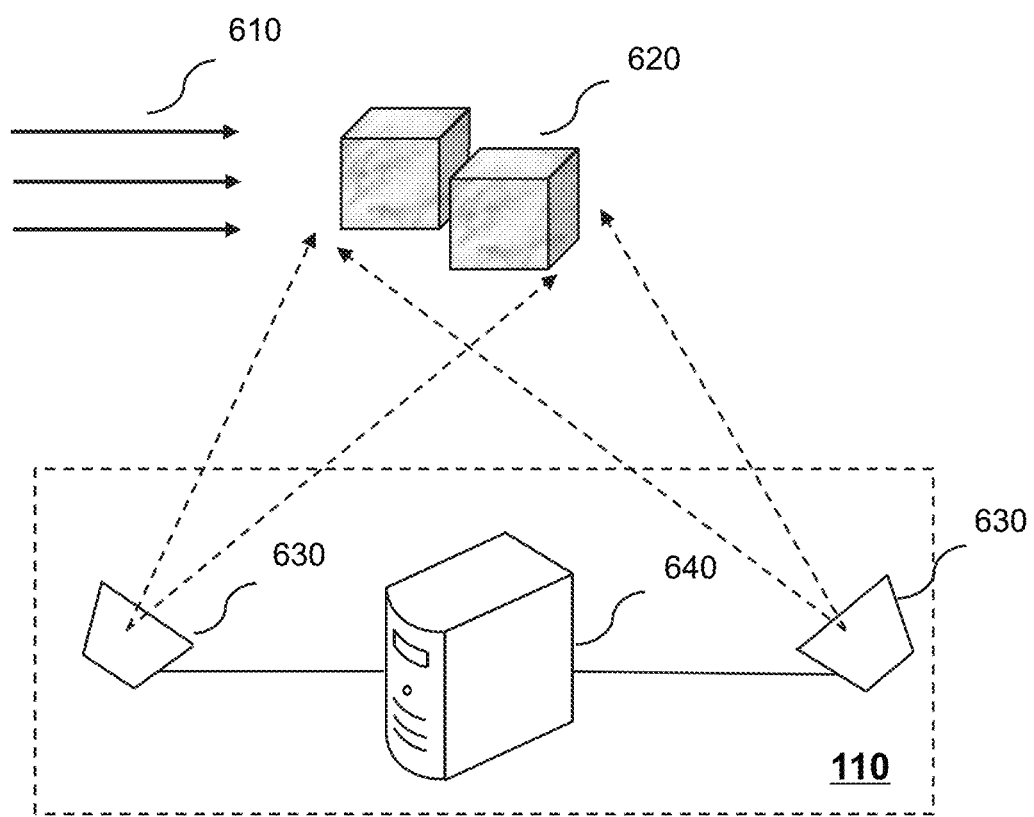
FIG. 6 is a schematic diagram illustrating obtaining image data according to some embodiments of the present disclosure.

FIG. 6 is a schematic diagram illustrating obtaining image data according to some embodiments of the present disclosure. The imaging device 110 may include one or more sensors 630 and a communication module 640. The imaging device 110 may obtain information of a scanning target 620 via the sensor 630. The obtained information may be transmitted to the remote processing device 120 or the local processing device 140 to be processed by the communication module 640 via the network 130. In some embodiments, the imaging device 110 may be a medical imaging device.

A signal source of the imaging device 110 may transmit a signal 610 to the scanning target 620. The signal 610 may be an X-ray, an electromagnetic wave, an ultrasonic wave, visible light, an electron, etc. In some embodiments, the signal 610 may interact with the scanning target 620. For example, the signal 610 may be reflected, refracted, or absorbed by the scanning target 620. In some embodiments, the signal 610 may excite a new signal during scanning the target. The signal(s) may be received by one or more sensors 630. In some embodiments, the direction in which the scanning target 620 and/or the signal 610 are incident may have a certain positional relationship with the position of the sensor 630 or the angle along which the signal is received. The signal received by the sensor 630 may include one or more features of the scanning target 620 and a background. The one or more features may be geometrical or textual features of the scanning target 620, background signal features, background brightness, background shadows, etc. The sensor 630 may generate image data based on the received signal. In some embodiments, the image data may include the one or more features. Information of the one or more features may be used for rendering the image data. In some embodiments, information of the one or more features of the background may be saved in one or more scene files.

Figure 7A:
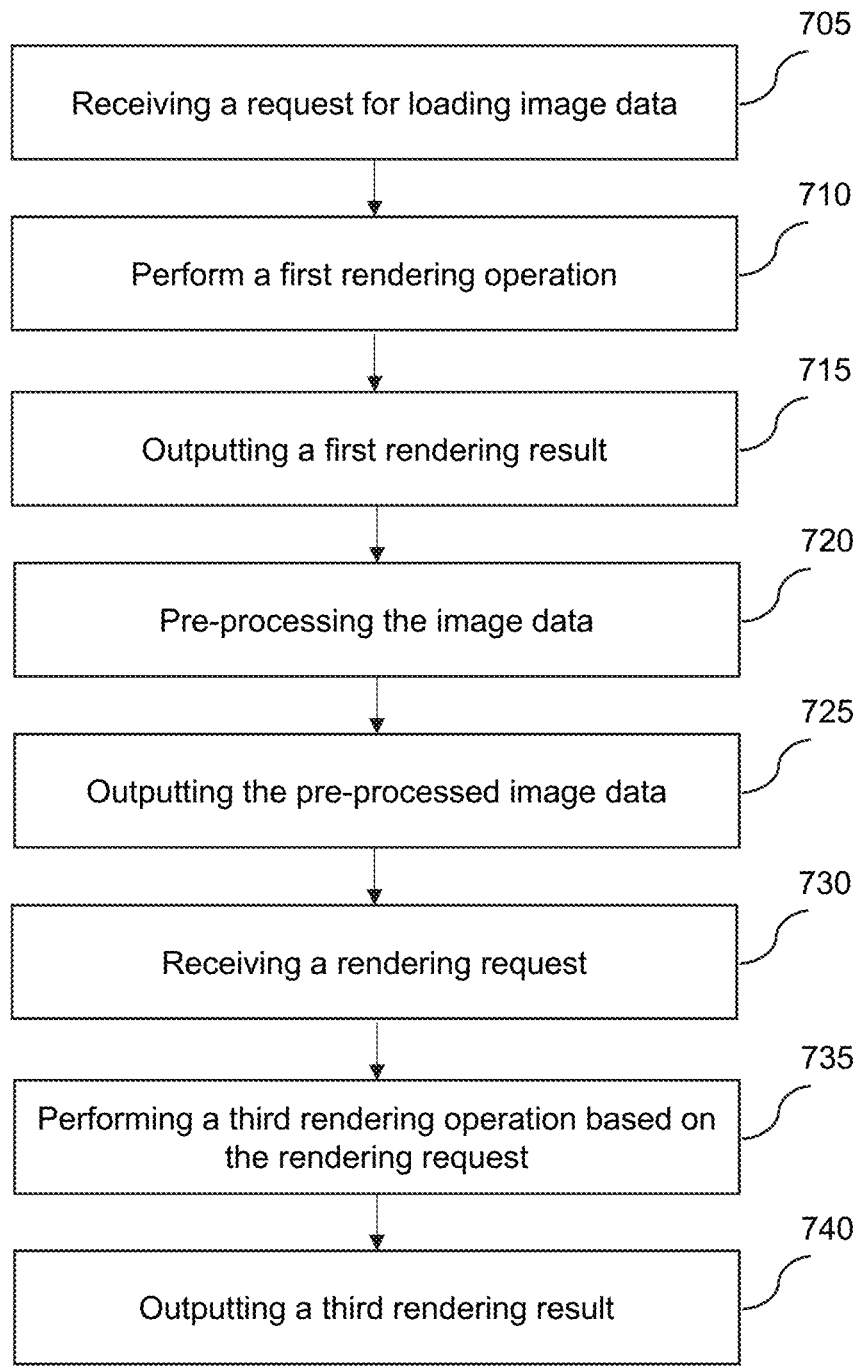
FIG. 7A is a flowchart illustrating an exemplary process for rendering image data according to some embodiments of the present disclosure.

FIG. 7A is a flowchart illustrating an exemplary process for rendering image data according to some embodiments of the present disclosure. In some embodiments, process 700 may be performed by the remote processing device 120.

Step 705 may include receiving a request for loading image data. In some embodiments, the request for loading the image data may be transmitted out by the local processing device 140. In some embodiments, the image data may be stored in the remote processing device 120 in advance, for example, in the storage module 240. In some embodiments, the image data may be obtained from other modules or devices in the system or storage devices outside the system via the input/output module 210 and/or the communication module 230. In some embodiments, the loading of the image data may include loading stored content(s) into the processing module 220 to be further processed.

Step 710 may include performing a first rendering operation on the loaded image data to generate a first rendering result. The implementation ways and definitions regarding a rendering operation may be found elsewhere in the present disclosure. In some embodiments, the first rendering result may be 2D or 3D images of a scanning target based on different light intensities, imaging angles, distances, surface shapes, shadows, etc. In some embodiments, the first rendering result may be a surface image of the scanning target. In some embodiments, the first rendering result may be the scanning target's cross-sectional image, internal image, etc.

Step 715 may include outputting the first rendering result. In some embodiments, step 715 may include transmitting the first rendering result to the local processing device 140 via the input/output module 210 and/or the communication module 230. In some embodiments, step 715 may include storing the first rendering result into the storage module 240.

Step 720 may include performing one or more pre-processing operations on the image data. The pre-processing operation may include filtering, noise reduction, smoothing, or the like, or a combination thereof. In some embodiments, the pre-processing operation may include downsampling and compressing the image data. For example, the pre-processing operation may include resampling the image data at a relatively low sampling rate to reduce the resolution of the image corresponding to the image data.

Step 725 may include outputting the pre-processed image data. In some embodiments, step 725 may include transmitting the pre-processed image data to the local processing device 140 via the input/output module 210 and/or the communication module 230. In some embodiments, step 725 may include storing the image data into the storage module 240. In some embodiments, the pre-processed image data may be matched with an output environment. For example, if the hardware configuration of the local processing device 140 is relatively low (e.g., the storage space is relatively small, the processing capacity is relatively weak), step 715 may include resampling the image data at a relatively low sampling rate to reduce the resolution and size of the image data, which may then reduce the requirement for storage space and calculation volume of the local processing device 140.

Step 730 may include receiving a rendering request. The rendering request may include information (e.g., light intensity, imaging angle, light source position) required for a rendering operation. In some embodiments, the rendering request may be transmitted out by the local processing device 140. In some embodiments, step 730 may further include receiving a request for performing one or more non-rendering operations. In some embodiments, the non-rendering operation may include a user's continuous operation, such as rotation, panning, mirroring, zooming, multi-planar reconstruction, window adjustment, etc. In some embodiments, step 730 may include receiving the image data that has been processed according to the one or more non-rendering operations. For example, the remote processing device 120 may first transmit the pre-processed image data to the local processing device 140 in step 725. After the local processing device 140 performs one or more non-rendering operations on the pre-processed image data, the processing device 120 may receive a rendering request and the image data that have been processed by the non-rendering operation(s) in step 730.

Step 735 may include performing a third rendering operation on the image data based on the received request for rendering to generate a third rendering result. In some embodiments, the third rendering operation may be the same as the first rendering operation. The methods for the implementation and definitions regarding a rendering operation may be found elsewhere in the present disclosure. In some embodiments, step 735 may further include performing a non-rendering operation on the image data based on the request for performing a non-rendering operation received in step 730. In some embodiments, the third rendering result may be 2D or 3D images of the scanning target based on different light intensities, imaging angles, distances, surface shapes, shadows, etc. In some embodiments, the third rendering result may be a surface image of the scanning target. In some embodiments, the third rendering result may be the scanning target's cross-sectional image, internal image, etc.

Step 740 may include outputting the third rendering result. In some embodiments, step 740 may include transmitting the third rendering result to the local processing device 140 via the input/output module 210 and/or the communication module 230. In some embodiments, step 740 may include storing the third rendering result into the storage module 240.

Figure 7B:
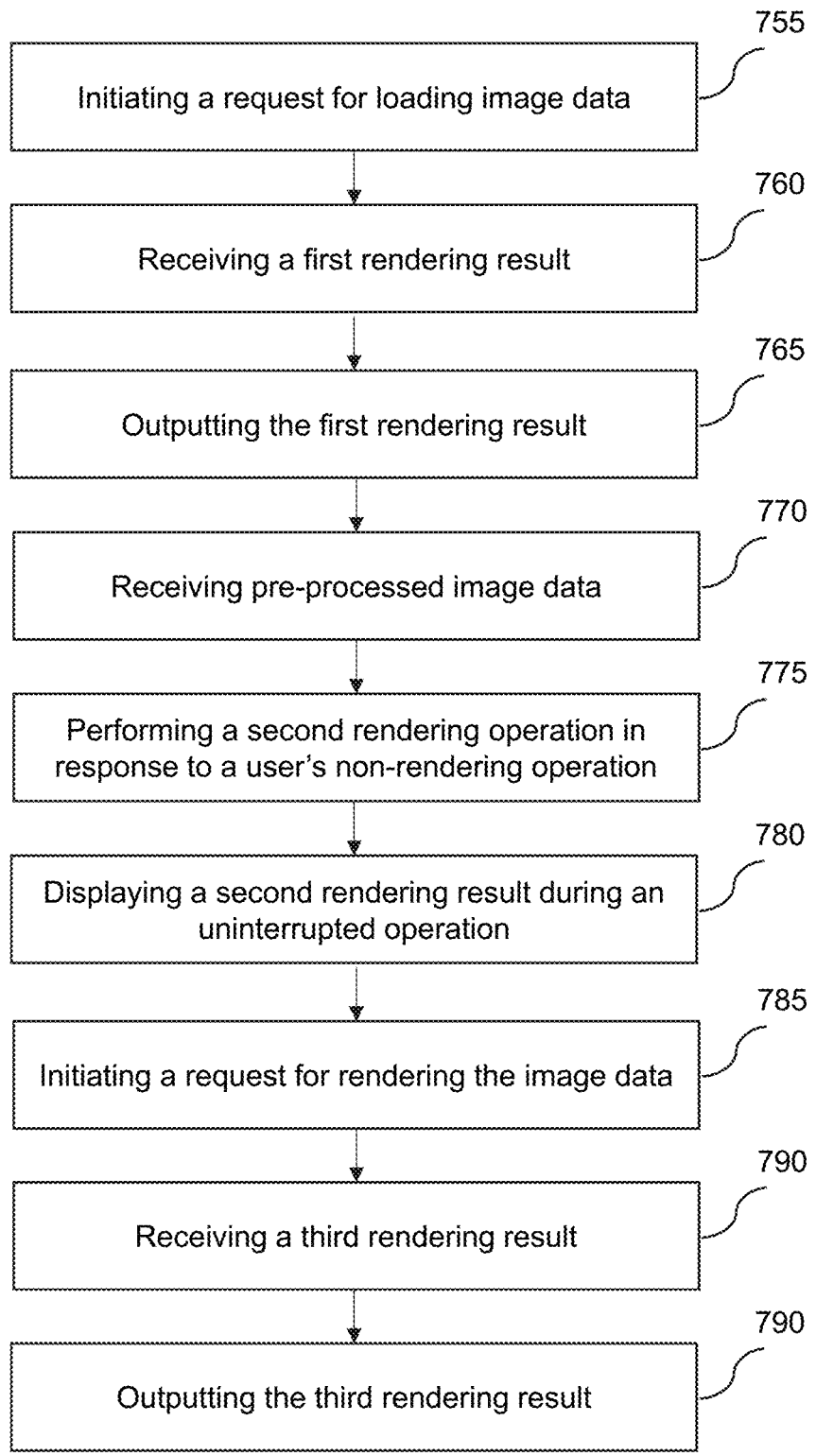
FIG. 7B is a flowchart illustrating an exemplary process for rendering image data according to some embodiments of the present disclosure.

FIG. 7B is a flowchart illustrating an exemplary process for rendering image data according to some embodiments of the present disclosure. In some embodiments, process 750 may be performed by the local processing device 140. In some embodiments, one or more steps of process 750 may correspond to one or more steps of process 700.

Step 755 may include initiating a request for loading image data. In some embodiments, the request for loading image data may be transmitted to the remote processing device 120. In some embodiments, the image data may be stored in the remote processing device 120 in advance, for example, in the storage module 240. In some embodiments, the image data may be obtained, via the input/output module 210 and/or the communication module 230, from the local processing device 140, other modules or devices of the system, storage devices outside the system, etc. In some embodiments, the loading of the image data may include loading the stored content(s) into the processing module 220 of the remote processing device 120 to be further processed.

Step 760 may include receiving a first rendering result. In some embodiments, the first rendering result may be output by the remote processing device 120 in step 715. In some embodiments, the first rendering result may be 2D or 3D images of a scanning target based on light intensities, imaging angles, distances, surface shapes, shadows, etc. In some embodiments, the first rendering result may be a surface image of the scanning target. In some embodiments, the first rendering result may be the scanning target's cross-sectional image, internal image, etc.

Step 765 may include outputting the first rendering result. In some embodiments, step 765 may include transmitting the first rendering result to other modules of the system or modules or devices outside the system via the input/output module 215 and/or the communication module 245. In some embodiments, step 765 may include displaying the first rendering result via a display component of the input/output module 215. In some embodiments, step 765 may include storing the first rendering result into the storage module 255.

Step 770 may include receiving pre-processed image data. In some embodiments, the pre-processed image data may be output by the remote processing device 120 in step 725. The image data may be obtained by a pre-processing operation in step 720. In some embodiments, the pre-processed image data may be image data with a relatively low sampling rate or a relatively low resolution. Further, the sampling rate of the pre-processed image data may be matched with the hardware configuration (e.g., storage space, processing capability) of the local processing device 140. For example, if the hardware configuration of the local processing device 140 is relatively low, the image data may be reduced to having a lower sampling rate by the pre-processing operation. In some embodiments, the hardware configuration may be input by a user via the input/output module 215. In some embodiments, the local processing device 140 may automatically detect and transmit its configuration information to the remote processing device 120. The remote processing device 120 may adjust the pre-processing operation according to the hardware configuration.

Step 775 may include receiving and responding to one or more non-rendering operations of a user and performing a second rendering operation on the pre-processed image data according to the non-rendering operation. In some embodiments, the non-rendering operation may include performing an adjustment operation (e.g., rotating, panning, zooming, mirroring, multi-planar reconstruction, window width, and window position adjustment) on the pre-processed image data. In some embodiments, the non-rendering operation may be a continuous operation. For example, when the local processing device 140 is involved, according to a user's settings, a left click, a middle click, and a right click of a mouse may be set as the beginning of the continuous operation (e.g., panning, rotation, zooming, window adjustment), a view matrix may be changed by dragging the mouse, and the continuous operation may be terminated by popping up the mouse. In some embodiments, the continuous operation may be terminated when the mouse is at rest for a long time, and a continuous operation state may be entered into when the mouse is dragged again. For example, when a tablet computer or a smartphone is involved, the beginning and the termination of a continuous operation may be determined based on an operation of a finger touch, sliding, stilling, a two-finger rotation, double finger zooming, etc. In some embodiments, the remote processing device 120 may transmit a first rendering result to the local processing device 140 in step 715. The remote processing device 120 may further transmit the pre-processed image data corresponding to the first rendering result to the local processing device 140 in step 725. The local processing device 140 may display the first rendering result via a display component of the input/output module 215. In some embodiments, a user may further perform an adjustment operation on the first rendering result displayed by the display component in step 775. In some embodiments, the local processing device 140 may perform a second rendering operation on the image data in accordance with the adjustment operation and generate a second rendering result. The second rendering result may be 2D or 3D images of a scanning target based on different light intensities, imaging angles, distances, surface shapes, shadows, etc.

Step 780 may include presenting the second rendering result during the non-rendering operation performed by the user. In some embodiments, the second rendering result may be displayed via a display component of the input/output module 215. In some embodiments, the non-rendering operation may be a continuous operation. Accordingly, the second rendering operation and the second rendering result may be real time.

Step 785 may include transmitting out a request for rendering image data. In some embodiments, the request for rendering image data may be transmitted to the remote processing device 120. In some embodiments, the rendering request may include information required for a rendering operation, such as light intensity, imaging angle, light source position, etc. In some embodiments, step 785 may further include transmitting out a request for one or more non-rendering operations. In some embodiments, the non-rendering operation may include a user's continuous operation including a rotation, a panning, a mirroring, a zooming, a multi-planar reconstruction, a window adjustment, etc. In some embodiments, step 785 may transmit out the non-rendered image data.

Step 790 may include receiving a third rendering result. In some embodiments, the third rendering result may be generated and transmitted by the remote processing device 120. In some embodiments, the third rendering result may be generated by performing a rendering operation on the non-rendered image data. The third rendering result may be 2D or 3D images of one or more scanning targets based on light intensities, imaging angles, distances, surface shapes, shadows, etc.

Step 795 may include outputting the third rendering result. In some embodiments, step 795 may include transmitting the third rendering result to other modules in the system or modules or devices outside the system via the input/output module 215 and/or the communication module 245. In some embodiments, step 795 may include displaying the third rendering result via a display component of the input/output module 215. In one embodiment, step 765 may include storing the third rendering result into the storage module 255.

Figure 8:
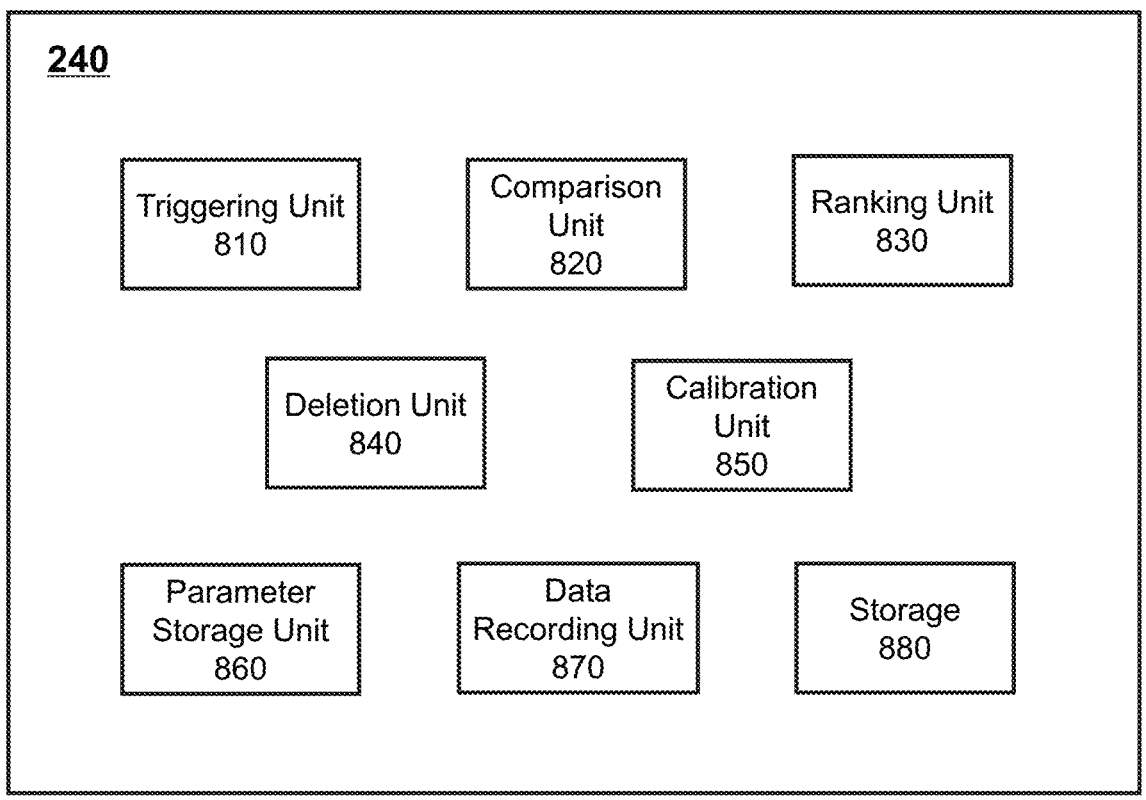
FIG. 8 is a schematic block diagram of a storage module according to some embodiments of the present disclosure.

FIG. 8 is a schematic block diagram of a storage module according to some embodiments of the present disclosure. The storage module 240 may include a triggering unit 810, a comparison unit 820, a ranking unit 830, a deletion unit 840, a calibration unit 850, a parameter storage unit 860, a data recording unit 870, and a storage 880.

The triggering unit 810 may generate a management signal of stored content. The management signal of stored content may include a scanning signal of remaining storage capacity, a deletion signal of stored content, a repairing signal of stored content, etc. In some embodiments, the data management signal generated by the triggering unit 810 may monitor and manage the stored contents in the storage 880. In some particular moments, the triggering unit 810 may generate the management signal of stored content. The particular moment may include a preset time, an activating time of the imaging system 100, a time point when a new storing operation is performed, a time point when the remaining capacity of the disk is lower than a threshold, etc. For example, the triggering unit 810 may trigger a scanning for remaining storage capacity when the imaging system 100 is powered on and subsequent each hour.

The comparison unit 820 may be configured for numerical value comparison or condition comparison. The comparison unit 820 may be configured to determine whether a numerical value reaches a preset threshold or whether a preset condition is satisfied. For example, the comparison unit 820 may be configured to compare the remaining capacity of the storage 880 with the size of a preset capacity threshold. For instance, the comparison unit 820 may be configured to determine whether the imaging system 100 has entered into a stage of frequent operation and mass storage. In some embodiments, the comparison between a certain numerical value and a threshold may be performed using a method of determining a difference, determining a quotient value, determining a reciprocal, etc. In some embodiments, the comparison unit 820 may include a programmable logic device (PLD), an application specific integrated circuit (ASIC), a central processing unit (CPU), a single chip microcomputer (SCM), a system on chip (SoC), etc.

The ranking unit 830 may rank a plurality of stored contents in the storage 880. The ranking unit 830 may perform a ranking based on one or more features. The one or more features may be related to the stored contents in the storage 880. In some embodiments, the feature may be storage time, the number of uses, the size of stored content, last use time of stored content, etc. In some embodiments, the ranking unit 830 may perform a ranking based on two features at the same time. For example, the ranking unit 830 may first perform a ranking in accordance with the number of uses of stored content. When there are a plurality of stored contents with the same number of uses, the ranking unit 830 may rank the data in accordance with a ratio of the storage time to the number of uses. In some embodiments, the ranking unit 830 may perform a ranking based on the last use time of stored content or a ratio of the storage time to the number of uses of stored content. According to the features, the ranking unit 830 may rank a plurality of stored contents using a sorting algorithm. The sorting algorithm may include an algorithm of insertion sorting, bubbling sorting, fast sorting, selection sorting, heap sorting, merge sorting, cardinality sorting, Hill sorting, etc. In some embodiments, the ranking unit 830 may select one or more sorting algorithms based on the requirement of computational load or time efficiency.

The deletion unit 840 may delete stored content(s) in the storage 880. The stored content(s) may be in a format of text, graphics, images, sounds, video, etc. In some embodiments, the stored content(s) in the storage 880 may be a construction rule that complies with the DICOM (Digital Imaging and Communications in Medicine) protocol. In some embodiments, a DICOM file may include complete information of a patient. The information may include basic information (e.g., name, sex, age, medical history) of the patient, medical images, related reports, etc. When the deletion unit 840 deletes a DICOM file, the deletion unit 840 may delete the complete DICOM file, delete medical images thereof, delete data elements thereof, delete other DICOM files with other types generated based on post-processing operations thereon, etc. In some embodiments, the deletion unit 840 may delete a complete DICOM file directly.

The calibration unit 850 may be configured for a threshold calibration. The threshold may include a remaining storage capacity threshold, a threshold of the number of uses of data, a storage time threshold of data, a ratio of storage time of the data to the number of uses of the data, etc. In some embodiments, when there is a threshold to be calibrated, the calibration unit 850 may perform an adaptive threshold adjustment, select from a plurality of preset thresholds, or asking for a user's input. In some embodiments, the calibration unit 850 may start the threshold calibration after receiving a trigger signal from the triggering unit 810.

The parameter storage unit 860 may store parameter(s) used for content management. In some embodiments, the parameter may be used to monitor and manage a plurality of stored contents in the storage 880, such as identifying and deleting a stored content, etc. In some embodiments, the parameter(s) stored in the parameter storage unit 860 may be a condition for triggering a scanning, a data deletion, or a data repair, a numerical range or a threshold for comparing the remaining capacity, a data feature for ranking, etc. The parameter(s) stored in the parameter storage unit 860 may be set by a user, preset by the system, or adaptively adjusted according to the current storage situation of the storage 880. For example, if the storage capacity of the storage 880 is still below the threshold after ranking and deleting the stored contents whose last use times are earlier than the preset time in accordance with the number of uses and the ratio of the storage time to the number of uses, the parameter storage unit 860 may set a smaller ratio of the storage time to the number of uses, and delete data whose ratio is higher than the set value to ensure adequate storage capacity.

The data recording unit 870 may record features of the stored contents in the storage 880. The features of the data may be provided to the ranking unit 830 that may be configured to rank the plurality of stored contents in the storage 880. In some embodiments, the features of the stored contents may include each stored content's number of uses, last use time, storage time, etc. In some embodiments, the number of uses and the last use time of the stored content may be obtained according to the number of times that a user has searched or viewed the stored content and the time points when the user has searched or viewed the stored content. In some embodiments, the number of uses and the last use time of the stored content may be obtained by the user by viewing or modifying a DICOM file. For example, when the user views a DICOM file, the storage 880 may receive a searching request from the user. According to a check information table, a sequence information table, and primary key UIDs (StudylnstanceUID, SerieslnstanceUID, and SopinstanceUID corresponding to the image information of the DICOM file, the storage 880 may search for relevant image information and increase the number of uses by 1 in a field where the number of uses of the DICOM file is recorded. Accordingly, the last use time of the stored content may be updated at the same time. In some embodiments, a storage time of a stored content may be obtained by calculating a time point when the stored content is created. In some embodiments, the data feature recorded in the data recording unit 870 may be synchronized to the ranking unit 830 and may be used as the basis for ranking a plurality of stored contents. In some embodiments, the data recording unit 870 may synchronize the features of all stored contents to the ranking unit 830 in real time or synchronize the features according to a preset time interval. In some embodiments, the data recording unit 870 may synchronize features of stored contents with the changes to the ranking unit 830 after each deletion.

The storage 880 may be configured to store information. The information may be derived from the medical imaging device 110, the network 130, the local processing device 140, etc. In some embodiments, the information in the storage 880 may include image data, rendered images, instructions input by a user, etc. In some embodiments, the image data and rendered images may be in the format of a DICOM file. A DICOM file may include DICOM file meta information and a DICOM data set. The DICOM file meta information may identify information such as file type, content, transmission format, etc. The DICOM data set may include patient's basic information (e.g., name, age, medical history), medical images, related reports, etc. In some embodiments, the DICOM data set may be stored by one or more data elements.

The storage 880 may include various types of storage devices such as a solid-state disk, a mechanical hard disk, a USB flash memory, an SD memory card, an optical disk, a random-access memory (RAM), a read-only memory (ROM), etc. In some embodiments, the storage 880 may include one or more mass storage devices, such as a mass storage array managed by one or more controllers.

It should be noted that the above description of the units in the storage module 240 merely provides some specific embodiments, and should not be considered as the only practical solution. It will be apparent to those skilled in the art that after understanding the basic principle of the units, various modifications and changes to the configuration of the storage module 240 may be made without departing from the principle. However, these modifications and changes are still within the scope of the present disclosure.

For example, the parameter storage unit 860 and the data recording unit 870 may be separate storage elements or devices (e.g., a register, a USB flash memory) or may be integrated into the storage 880 (e.g., performed via one or more partitions of the storage 880).

Figure 9:
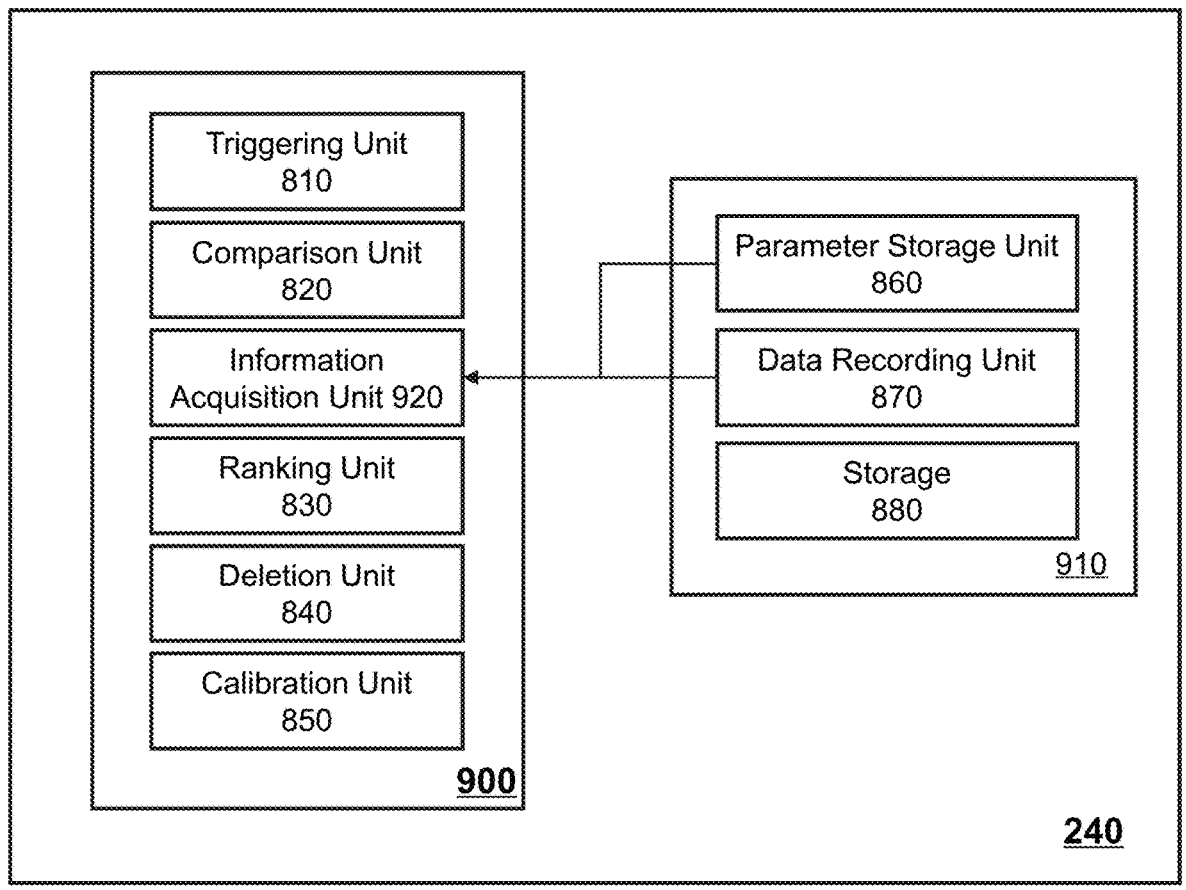
FIG. 9 is a schematic block diagram of a storage module according to some embodiments of the present disclosure.

FIG. 9 is a schematic block diagram of a storage module according to some embodiments of the present disclosure. As shown in FIG. 9, the storage module 240 may be distributed in the remote processing device 900 and the remote processing device 910. The remote processing device 900 may include a triggering unit 810, a comparison unit 820, a ranking unit 830, a deletion unit 840, a calibration unit 850, and an information acquisition unit 920. The remote processing device 910 may include a parameter storage unit 860, a data recording unit 870, and a storage 880.

The characteristics and functions of the triggering unit 810, the comparison unit 820, the ranking unit 830, the deletion unit 840, the calibration unit 850, the parameter storage unit 860, the data recording unit 870, and the storage 880 may be found elsewhere in the present disclosure, for example, FIG. 8 and the description thereof.

The remote processing device 900 and the remote processing device 910 may be connected to each other directly or via a network. The remote processing device 900 and 910 may be a file server, a database server, a network storage server, or a specially designed server with one or more special functions. In some embodiments, the remote processing device 900 may be a WEB 3D server. The WEB 3D server may include an input/output module, a processing module, a communication module, a configuration information module, a storage module, etc. In some embodiments, the remote processing device 910 may be a Picture Archiving and Communication System (PACS) server. The PACS server may include an input/output module, a processing module, a communication module, etc.

The information acquisition unit 920 may acquire information from the remote processing device 910. The information acquisition unit 920 may acquire information from the parameter storage unit 860 and the data recording unit 870. In some embodiments, the information acquisition unit 920 may transmit the acquired information to other units of the remote processing device 900. In some embodiments, the information acquisition unit 920 may transmit the information acquired from the parameter storage unit 860 to the triggering unit 810. In some embodiments, the information acquisition unit 920 may transmit the information acquired from the data recording unit 870 to the ranking unit 830. In some embodiments, the information acquisition unit 920 may acquire information from the remote processing device 910 in real time or acquire information according to a preset time interval. In some embodiments, the information acquisition unit 920 may synchronize information after completing a data deletion.

In some embodiments, the remote processing device 900 may be replaced by a local processing device, such as the local processing device 140. Further, the parameter storage unit 860 may be included in the local processing device 140.

Figure 10:
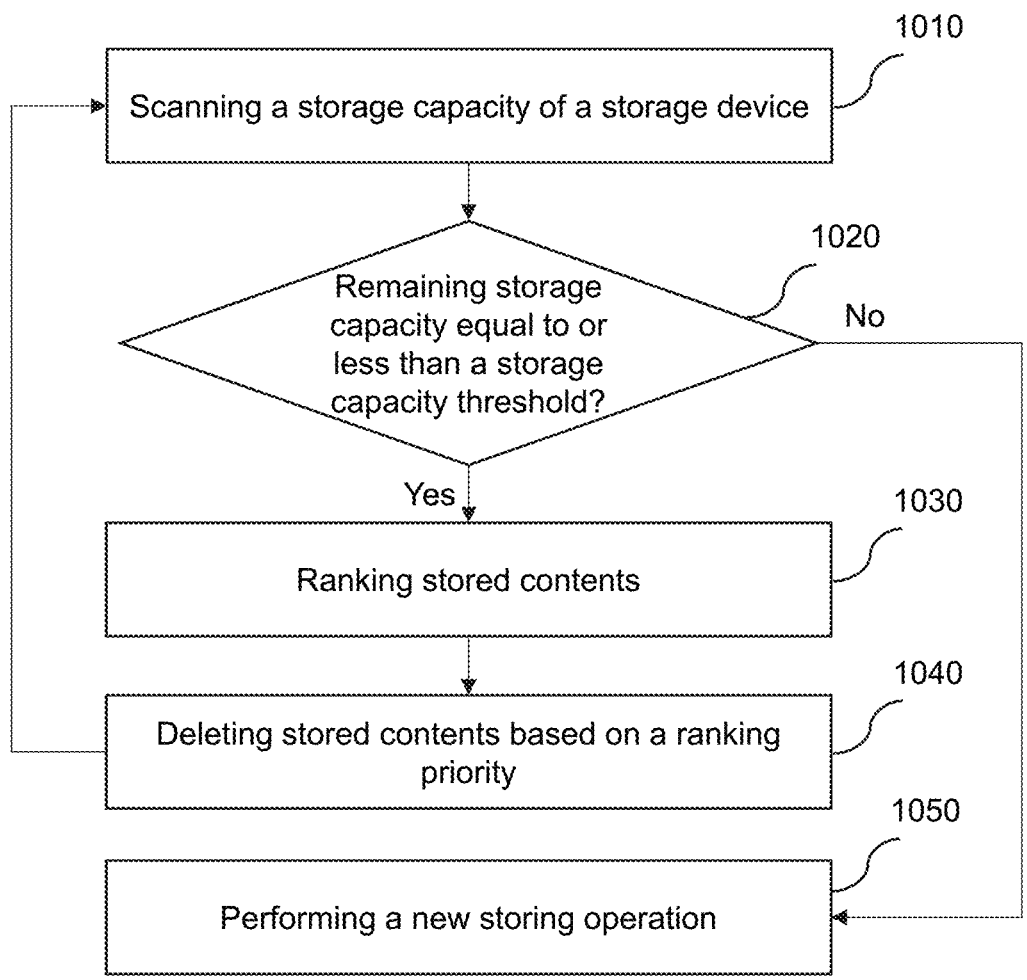
FIG. 10 is a flowchart illustrating an exemplary process for deleting data according to some embodiments of the present disclosure.

FIG. 10 is a flowchart illustrating an exemplary process for deleting data according to some embodiments of the present disclosure. In some embodiments, the process 1000 may be performed by the storage module 240 of the remote processing device 120.

Step 1010 may include scanning a capacity of a storage device. In some embodiments, the scanning may include obtaining capacity information of the storage device. The capacity information may include total capacity, used capacity, remaining capacity, used percentage, remaining percentage, remaining available time, etc. In some embodiments, the storage device may send out a signal including the capacity information itself, and the signal may be further received and analyzed by the processing module 220. In some embodiments, the remote processing device 120 may measure the storage device to obtain the capacity information of the storage device. In some embodiments, the remote processing device 120 may include a timing component. The timing component may control the occurrence of a triggering signal. The triggering signal may initiate a measurement of the capacity information of the storage device. Further, the timing component may transmit out a triggering signal every once in a while to continuously detect the capacity information of the storage device. For example, the timing component may control the remote processing device 120 to detect the capacity information of the storage device by transmitting out a triggering signal every time when the device is powered on and subsequent each hour. In some embodiments, a user may change the time interval of the measurement via the inputting/output module 210, the input/output module 215, or other ways, etc. In some embodiments, the remote processing device 120 may detect the capacity information of the storage device at each time when the storage device performs a storage.

Step 1020 may include comparing the remaining capacity of the storage device with a capacity threshold. In some embodiments, the capacity threshold may be pre-stored in the storage module 240. In some embodiments, the capacity threshold may be obtained from the local processing device 140 via the input/output module 210. In some embodiments, the capacity threshold may be provided by a user via the input/output module 210 or the input/output module 215. In some embodiments, if the remaining capacity of the storage device is greater than the capacity threshold, the storage module 240 may perform a new storing operation in step 1050. In some embodiments, if the remaining capacity of the storage device is less than the capacity threshold, the storage module 240 may delete a part of the stored contents in step 1030 and/or step 1040 to increase the remaining capacity.

Step 1030 may include ranking the stored contents in the storage device. In some embodiments, the ranking of the stored contents may be based on one or more features of the stored contents, such as storage time, last use time, the number of uses, size, user name, type, etc. In some embodiments, the storage device may generate a ranking table of the stored contents based on the ranking. Further, the storage device may generate a global ranking based on a plurality of rankings. For example, a plurality of scores or weights may be assigned to the plurality of rankings, the plurality of rankings may be summed based on the plurality of scores or weights, then the global ranking may be generated. In some embodiments, the ranking of the stored contents may be based on a ratio of the plurality of features of the stored contents. For example, the stored contents may be ranked according to a ratio of the storage time to the number of uses. In some embodiments, the ranking may indicate a priority of deletion. For example, after the stored contents are ranked based on the storage time, a priority of deletion of the stored content with an earlier storage time may be higher. When the remaining storage capacity is insufficient, the stored content with an earlier storage time may be preferentially deleted.

Step 1040 may include sequentially deleting the stored contents based on the priorities of the ranking. If priorities of deletion of a plurality of stored contents are the same, the plurality of stored contents may be deleted at the same time. In some embodiments, after the stored content with the highest or a relatively high priority of deletion is deleted according to a ranking, the storage capacity of the storage device may be scanned in step 1010. If the remaining capacity of the storage device is still less than the capacity threshold, the stored content with the highest or a relatively high priority of deletion according to the same ranking or another ranking may be deleted in step 1040. In some embodiments, the storage device may obtain a difference between the remaining capacity of the storage device and the capacity threshold in step 1020. Further, step 1040 may include accumulating capacities of the deleted contents of each deletion and comparing the accumulated capacity with the difference. Step 1040 may include deleting the stored contents of the storage device in turn according to the priorities of deletion of the ranking until the accumulated capacity of the deleted stored contents is greater than the difference.

Figure 11:
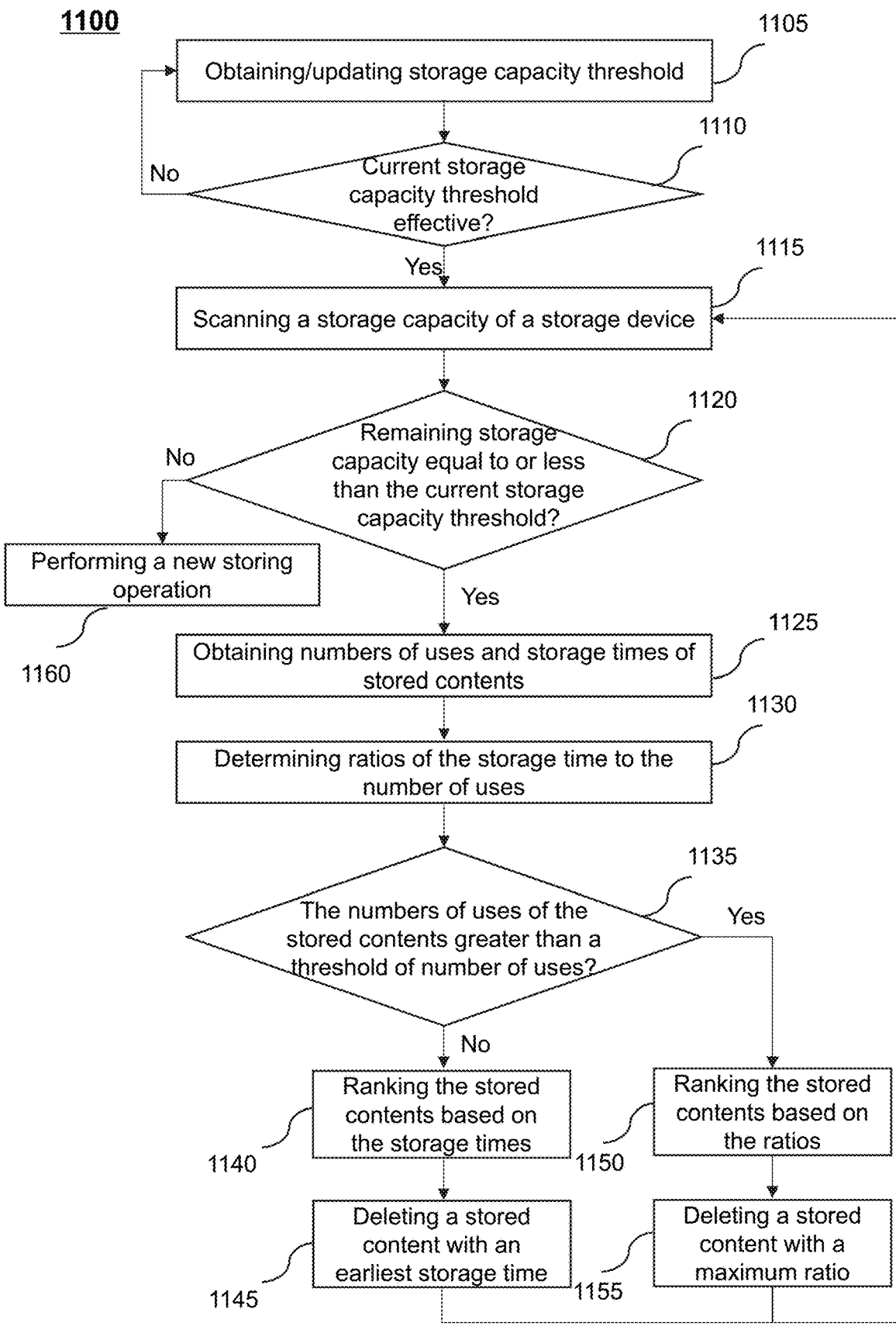
FIG. 11 is a flowchart illustrating an exemplary process for deleting data according to some embodiments of the present disclosure.

FIG. 11 is a flowchart illustrating an exemplary process for deleting data according to some embodiments of the present disclosure. In some embodiments, process 1100 may be performed by the storage module 240 of the remote processing device 120.

Step 1105 may include obtaining a capacity threshold. In some embodiments, the capacity threshold may be obtained from the storage module 240. In some embodiments, the capacity threshold may be obtained from the local processing device 140 via the input/output module 210. In some embodiments, the capacity threshold may be provided by a user via the input/output module 210. In some embodiments, the capacity threshold may be a percentage ratio or a size. For example, the capacity threshold may be 50%, 200 MB, etc. In some embodiments, the capacity threshold may be a plurality of percentage ratios or sizes. When the remaining capacity of the storage space is respectively less than the plurality of percentage ratios or sizes, the storage device may perform one or more operations described elsewhere in the present disclosure.

Step 1110 may include determining whether the capacity threshold is valid. In some embodiments, the determination of the validity may include determining whether the capacity threshold is within a reasonable range, for example, whether the percentage of the capacity threshold is between 0 and 100% or whether the size of the capacity threshold is between 0 and the maximum capacity of the storage device. If the capacity threshold is determined to be an invalid threshold, process 1100 may return to step 1105 to update the capacity threshold. If the capacity threshold is determined to be a valid threshold, process 1100 may proceed to step 1115. In some embodiments, step 1110 may include setting a calibration value and calibrating the capacity threshold by the calibration value. The calibration value may be used to automatically calibrate the threshold, in order to avoid the set threshold from being too large, which may result in erroneous deletion of some important data. The subsequent steps of process 1100 may include determining whether to delete a part of the stored contents in the storage device based on a comparison result between the remaining capacity of the storage device and the capacity threshold. The deletion may be based on a particular ranking, such as a ranking based on storage time, last use time, the number of uses, size, etc. In some embodiments, the calibration value may be associated with a feature. For example, the calibration value may be that the number of uses is 10 times, the last use time is 24 Aug. 2015, etc. In some embodiments, when the capacity is insufficient, the storage device may sequentially delete the stored contents in accordance with the ranking. When a feature of a deleted stored content reaches the calibration value, if the remaining capacity of the storage device is greater than the capacity threshold, the capacity threshold may not be calibrated. Otherwise, the capacity threshold may be calibrated, and the current remaining capacity may be determined as a new capacity threshold. For example, if the stored contents are deleted according to the ranking of the number of uses, the stored contents with the numbers of use 0, 1, 2, 3, . . . may be sequentially deleted. When the number of uses of a deleted stored content reaches the calibration value of "10," a determination may be performed. If the remaining capacity is greater than the capacity threshold, the capacity threshold may not be calibrated. If the remaining capacity is less than or equal to the capacity threshold, in order to avoid erroneous deletion of the stored contents with a relatively high number of uses that is greater than "10," the deletion may be stopped, and the current remaining capacity may be determined as the new capacity threshold.

Step 1115 may include scanning the storage capacity of the storage device. In some embodiments, the scanning may include obtaining capacity information of the storage device. The capacity information may include total capacity, used capacity, remaining capacity, used percentage, remaining percentage, remaining available time, etc. In some embodiments, the storage device may transmit out a signal including the capacity information itself, and the signal may be further received and analyzed by the processing module 220. In some embodiments, the remote processing device 120 may measure the storage device to obtain the capacity information of the storage device. In some embodiments, the remote processing device 120 may include a timing component. The timing component may control the occurrence of a triggering signal. The triggering signal may initiate a measurement of the capacity information of the storage device. Further, the timing component may send out a triggering signal every once in a while to continuously detect the capacity information of the storage device. For example, the timing component may control the remote processing device 120 to detect the capacity information of the storage device by sending out a triggering signal every time when the device is powered on and subsequent each hour. In some embodiments, a user may change the time interval of the measurement via the inputting/output module 210, the input/output module 215, or other ways, etc. In some embodiments, the remote processing device 120 may detect the capacity information of the storage device at each time when the storage device performs a storage.

Step 1120 may include comparing the remaining capacity of the storage device with a capacity threshold. If the remaining capacity of the storage device is greater than the capacity threshold, the storage module 240 may perform a new storing operation in step 1160. In some embodiments, if the remaining capacity of the storage device is less than the capacity threshold, the storage module 250 may delete a part of the stored contents in subsequent steps of process 1100 to increase the remaining capacity.

Step 1125 may include obtaining the numbers of use, storage times of the stored contents in the storage device. In some embodiments, step 1125 may also include obtaining one or more other features of the stored contents, such as last use times, sizes, user names, types, etc.

Step 1130 may include determining ratios of the storage times to the numbers of use of the stored contents. In some embodiments, the storage time may be converted to a value in seconds or hours, and the ratio of the storage time value to the number of uses may be calculated. For example, a storage time "3 days 3 hours 24 minutes 30 seconds" may be converted to: $30+(24+(3+3*24)*60)*60)=271470$ (seconds). If the number of uses is 3 times, the ratio of the storage time value to the number of uses is: $271470/3=90490$. In some embodiments, step 1130 may also include determining ratios of the plurality of features.

Step 1135 may include comparing the numbers of uses of the stored contents with a threshold of number of uses. In some embodiments, the threshold of number of uses may be obtained from the storage module 240. In some embodiments, the threshold of number of uses may be obtained from the local processing device 140 via the input/output module 210. In some embodiments, the threshold of number of uses may be provided by a user via the input/output module 210 or the input/output module 215. In some embodiments, the threshold of number of uses may be a number (including 0). If the numbers of use of the stored contents are less than or equal to the threshold of number of uses, step 1140 may be performed. Otherwise, step 1150 may be performed.

Step 1140 may include ranking the stored contents in accordance with the storage time.

Step 1145 may include deleting the stored content with the earliest storage time according to the ranking result of the storage times of the stored contents. If storage times of a plurality of stored contents are the same, the plurality of stored contents may be deleted at the same time. In some embodiments, the storage capacity of the storage device may be scanned in step 1115 after the stored content with the earliest storage time is deleted according to the ranking result. If the remaining capacity of the storage device is still less than the capacity threshold, the stored content with the earliest or a relatively early storage time may be further deleted in step 1145. In some embodiments, the storage device may obtain a difference between the remaining capacity of the storage device and the capacity threshold in step 1115. Further, step 1115 may include accumulating capacities of the deleted stored contents of each deletion and comparing the accumulated capacity with the difference. Step 1145 may include deleting the stored content with the earliest storage time according to the ranking result of the storage times until the accumulated capacity of the deleted stored contents is greater than the difference.

Step 1150 may include ranking the stored contents according to the ratio of the storage time to the number of uses.

Step 1155 may include deleting the stored content with the highest ratio according to the ranking result of the ratios of the stored contents. If ratios of a plurality of stored contents are the same, the plurality of stored contents may be deleted at the same time. In some embodiments, the storage capacity of the storage device may be scanned in step 1115 after deleting the stored content with the highest ratio according to the ranking result of the ratios. If the remaining capacity of the storage device is still less than the capacity threshold, the stored content with the highest ratio or a relatively high ratio may be further deleted in step 1155. In some embodiments, the storage device may obtain a difference between the remaining capacity of the storage device and the capacity threshold in step 1115. Further, step 1115 may include accumulating capacities of the deleted stored contents of each deletion and comparing the accumulated capacity with the difference. Step 1155 may include deleting the stored content with the highest ratio of the storage time to the number of uses in accordance with the ranking result of the storage times until the accumulated capacity of the deleted stored contents is greater than the difference.

The above description is merely a specific embodiment of the present disclosure and should not be considered as the only embodiment. It will be apparent to those skilled in the art that, after understanding the contents and principles of the present disclosure, various modifications and changes in forms and details may be made without departing from the principles and constructions of the present disclosure. However, these modifications and changes are still within the scope of the present disclosure. In some embodiments, process 1000 and process 1100 may further include setting a threshold of last use time and comparing the last use times of the stored contents with the threshold. Process 1000 and process 1100 may perform different deletion processes based on the comparison result according to the ranking methods described in the various embodiments of the present disclosure. For example, if the last use time of a stored content is later than the threshold of last use time, it may indicate that the stored content has been recently used. Process 1000 and process 1100 may reduce the priority of deletion of the stored content.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, various aspects of the present disclosure may be performed entirely by hardware and may be performed entirely by software (including firmware, resident software, microcode), or may be implemented by a combination of both. The above hardware or software may be referred to as "data block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A method implemented on at least one machine, wherein each of the at least one machine having at least one processor and one storage, the method comprising:
    obtaining, by the at least one processor, capacity information of the storage, the capacity information including a remaining capacity of the storage;
    determining, by the at least one processor, the remaining capacity of the storage is equal to or less than a capacity threshold;
    ranking stored contents in the storage based on one or more features of the stored contents after determining that the remaining capacity of the storage is equal to or less than the capacity threshold; and
    deleting at least part of the stored contents based on the ranking, wherein the one or more features of the stored contents include number of uses, storage time, latest use time, or size, and the ranking the stored contents based on one or more features of the stored contents includes:
determining a threshold of number of uses;
determining there is no stored content whose number of uses is equal to or less than the threshold of number of uses; and
ranking the stored contents based on a ratio of the storage time to the number of uses.

2. The method of claim 1, wherein the at least one processor obtains the capacity information by a measurement operation on the storage initiated by a triggering signal.

3. The method of claim 2, wherein the triggering signal is transmitted when the machine is powered on and subsequent every preset time period, or when the storage performs a storing or deleting operation.

4. The method of claim 1, further comprising:
determining whether the capacity threshold is valid; and
in response to the determination that the capacity threshold is invalid, update the capacity threshold.

5. The method of claim 1, wherein the capacity threshold includes a percentage ratio or a size of storage capacity.

6. The method of claim 1, wherein the deleting a part of the stored contents based on the ranking comprises: deleting the stored content with the highest ratio.

7. A system, comprising:
a storage medium storing executable instructions, and
at least one processor in communication with the storage medium, when executing the executable instructions, causing the system to implement a method comprising:
obtaining, by the at least one processor, capacity information of the storage, the capacity information including a remaining capacity of the storage;
determining, by the at least one processor, the remaining capacity of the storage is equal to or less than a capacity threshold;
ranking stored contents in the storage based on one or more features of the stored contents after determining that the remaining capacity of the storage is equal to or less than the capacity threshold; and
deleting at least part of the stored contents based on the ranking, wherein the one or more features of the stored contents include number of uses, storage time, latest use time, or size, and the ranking the stored contents based on one or more features of the stored contents includes:
determining a threshold of number of uses;
determining there is no stored content whose number of uses is equal to or less than the threshold of number of uses; and
ranking the stored contents based on a ratio of the storage time to the number of uses.

8. The system of claim 7, wherein the at least one processor obtains the capacity information by a measurement operation on the storage initiated by a triggering signal.

9. The system of claim 7, the method further comprising:
determining whether the capacity threshold is valid; and
in response to the determination that the capacity threshold is invalid, update the capacity threshold.

10. The system of claim 7, wherein the capacity threshold includes a percentage ratio or a size of storage capacity.

11. A non-transitory computer readable medium including executable instructions that, when executed by at least one processor, cause the at least one processor to effectuate a method comprising:
obtaining, by the at least one processor, capacity information of the storage, the capacity information including a remaining capacity of the storage;
determining, by the at least one processor, the remaining capacity of the storage is equal to or less than a capacity threshold;
ranking stored contents in the storage based on one or more features of the stored contents after determining that the remaining capacity of the storage is equal to or less than the capacity threshold; and
deleting at least part of the stored contents based on the ranking, wherein the one or more features of the stored contents include number of uses, storage time, latest use time, or size, and the ranking the stored contents based on one or more features of the stored contents includes:
determining a threshold of number of uses;
determining there is no stored content whose number of uses is equal to or less than the threshold of number of uses; and
ranking the stored contents based on a ratio of the storage time to the number of uses.

\* \* \* \* \*